(12) United States Patent
Thiele et al.

(10) Patent No.: US 9,314,540 B2
(45) Date of Patent: Apr. 19, 2016

(54) COMPOUNDS FOR USE IN IMAGING, DIAGNOSING AND/OR TREATMENT OF DISEASES OF THE CENTRAL NERVOUS SYSTEM

(75) Inventors: Andrea Thiele, Bernau (DE); Georg Kettschau, Berlin (DE); Tobias Heinrich, Berlin (DE); Lutz Lehmann, Berlin (DE); Christer Halldin, Stockholm (SE); Sangram Nag, Huddinge (SE); Andrea Varrone, Bromma (SE); Balazs Gulyas, Solna (SE)

(73) Assignee: PIRAMAL IMAGING SA, Matran (CH)

( * ) Notice: Subject to any disclaimer, the term of this patent is extended or adjusted under 35 U.S.C. 154(b) by 142 days.

(21) Appl. No.: 13/880,847

(22) PCT Filed: Oct. 17, 2011

(86) PCT No.: PCT/EP2011/068124
§ 371 (c)(1),
(2), (4) Date: Aug. 30, 2013

(87) PCT Pub. No.: WO2012/052409
PCT Pub. Date: Apr. 26, 2012

(65) Prior Publication Data
US 2013/0336890 A1     Dec. 19, 2013

(30) Foreign Application Priority Data
Oct. 22, 2010 (EP) .................................... 10188559

(51) Int. Cl.
*C07C 211/29* (2006.01)
*A61K 51/04* (2006.01)
*C07B 59/00* (2006.01)

(52) U.S. Cl.
CPC ............... *A61K 51/04* (2013.01); *C07B 59/001* (2013.01); *C07C 211/29* (2013.01)

(58) Field of Classification Search
None
See application file for complete search history.

(56) References Cited

U.S. PATENT DOCUMENTS

2009/0191129 A1  7/2009  Lehmann et al.
2010/0233086 A1  9/2010  Lehmann et al.

FOREIGN PATENT DOCUMENTS

EP  2053033 A1  4/2009

OTHER PUBLICATIONS

Vippagunta et al. "Crystalline Solids," Advanced Drug Delivery Reviews, 2001, 48, pp. 18.*
Müller, Inorganic Chemistry, p. 14-15, 1993.*
International Search Report for PCT/EP2011/068124 (Jan. 9, 2012).
International Preliminary Report on Patentability for PCT/EP2011/068124 (Apr. 23, 2013).
(Continued)

*Primary Examiner* — Ernst V Arnold
*Assistant Examiner* — Jianfeng Song
(74) *Attorney, Agent, or Firm* — Millen, White, Zelano & Branigan, P.C.

(57) ABSTRACT

This invention relates to novel compounds suitable as precursors for the preparation of certain $^{18}$F labelled positron emission tomography (PET) tracers. Furthermore the invention relates to the preparation of such precursor molecules and to the preparation of PET tracers by $^{18}$F labelling of such precursors.

19 Claims, 9 Drawing Sheets

(56) References Cited

OTHER PUBLICATIONS

J.S. Fowler et al., "Selective Reduction of Radiotracer Trapping by Deuterium Substitution: Comparison of Carbon-11-L-Deprenyl and Carbon-11-Deprenyl-D2 for MAO B Mapping", Journal of Nucl. Med., vol. 36, No. 7 (1995) pp. 1255-1262.

J.S. Fowler et al., "Mechanistic Positron Emission Tomography Studies: Demonstration of a Deuterium Isotope Effect in the Monoamine Oxidase-Catalyzed Binding of [11C]L-Deprenyl in Living Baboon Brain", Journal of Neurochemistry, vol. 51, No. 5 (1988) pp. 1524-1534.

Roger Grant et al., "Containing the Words Generally Used in Chemistry, and Many of the Terms Used in the Related Sciences of Physics, Medicine, Engineering, Biology, Pharmacy, Astrophysics, Agriculture, Mineralogy, etc.", Grant & Hackh's Chemical Dictionary, Fifth Edition, p. 542 (1987).

Ex Parte Cai et al., USPTO Decision on Appeal in U.S. Appl. No. 11/852,433 (Appeal No. 2011-005302), pp. 1-18.

Ex Parte Liu et al., USPTO Decision on Appeal in U.S. Appl. No. 10/820,647 (Appeal No. 2009-015302), pp. 1-16.

* cited by examiner

Fig. 9
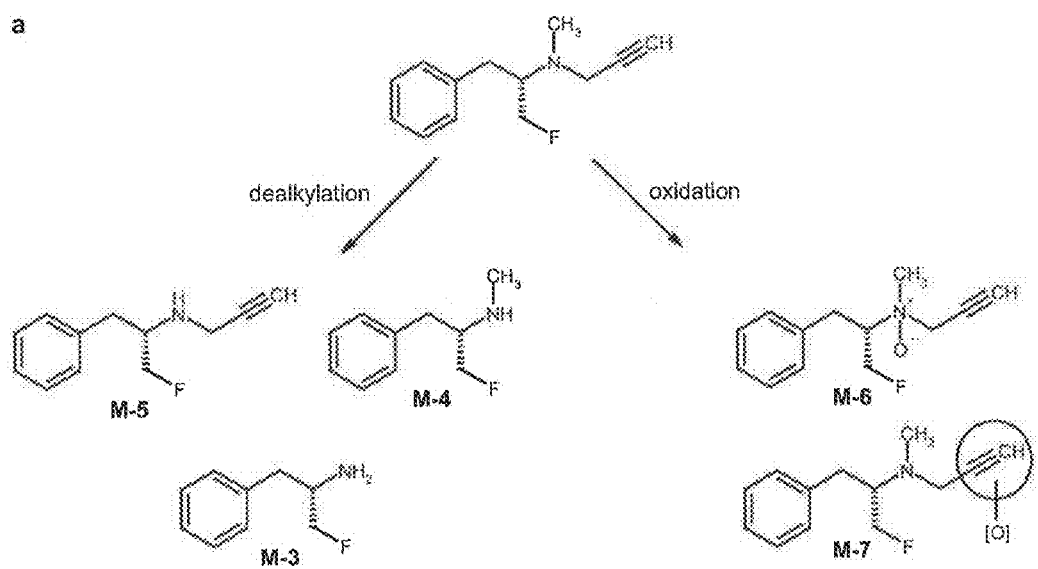
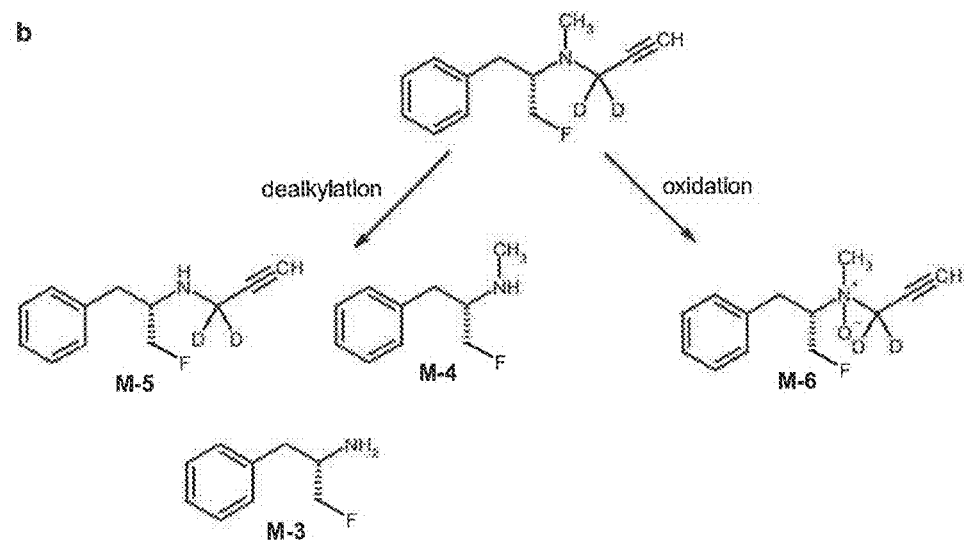

COMPOUNDS FOR USE IN IMAGING, DIAGNOSING AND/OR TREATMENT OF DISEASES OF THE CENTRAL NERVOUS SYSTEM

FIELD OF THE INVENTION

This invention relates to novel compounds suitable for labelling or already labelled by $^{18}$F, methods of preparing such compounds, compositions comprising such compounds, kits comprising such compounds or compositions and uses of such compounds, compositions or kits for diagnostic imaging by positron emission tomography (PET).

BACKGROUND AND PRIOR ART

Molecular imaging has the potential to detect disease, disease progression or therapeutic effectiveness earlier than most conventional methods in the fields of oncology, neurology and cardiology. Of the several promising molecular imaging technologies having been developed such as optical imaging, magnetic resonance imaging (MRI), single photon emission computed tomography (SPECT), and positron emission tomography (PET), PET is also of particular interest for drug development because of its high sensitivity and ability to provide quantitative and kinetic data.

For example positron emitting isotopes include carbon, iodine, fluorine, nitrogen, and oxygen. These isotopes can replace their non-radioactive counterparts in target compounds to produce tracers that function biologically and are chemically identical to the original molecules for PET imaging, or can be attached to said counterparts to give close analogues of the respective parent effector molecule. Among these isotopes, $^{18}$F is the most convenient labelling isotope due to its relatively long half life (110 min) which permits the preparation of diagnostic tracers and subsequent study of biochemical processes. In addition, its low $\beta^+$ energy (634 keV) is also advantageous.

The nucleophilic aromatic and aliphatic [$^{18}$F]-fluoro-fluorination reaction is of great importance for [$^{18}$F]-fluoro-labelled radiopharmaceuticals which are used as in vivo imaging agents targeting and visualizing diseases, e.g. solid tumours or diseases of brain. A very important technical goal in using [$^{18}$F]-fluoro-labelled radiopharmaceuticals is the quick preparation and administration of the radioactive compound.

Monoamine oxidases (MAO, EC, 1.4.3.4) represent a distinct class of amine oxidases. Monoamine oxidases are present in two isoforms known as MAO-A and MAO-B (Med. Res. Rev. 1984, 4: 323-358). Crystal structures of MAO-A and MAO-B complexed by ligands have been reported (J. Med. Chem. 2004, 47: 1767-1774 and Proc. Nat. Acad. Sci. USA 2005, 102: 12684-12689).

In the human brain the presence of MAO-B predominates over MAO-A. Cerebral MAO-B levels increase with age and are further up-regulated in the brains of Alzheimer's disease (AD) patients mostly due to an increase of reactive astrocytes. As astrocyte activity and, consequently, the activity of the MAO-B system is up-regulated in neuroinflammatory processes, radiolabelled MAO-B inhibitors may serve as an imaging biomarker in neuroinflammation and neurodegeneration, including Alzheimer's disease.

Inhibitors that are selective for either MAO-A or MAO-B have been identified and investigated (e.g. J. Med. Chem. 2004, 47: 1767-1774 and Proc. Nat. Acad. Sci. USA, 2005, 102: 12684-12689).

Deprenyl (compound A), a MAO-B inhibitor (Biochem. Pharmacol. 1972, 5: 393-408) and clorgyline (B), a MAO-A inhibitor (Acta Psychiatr. Scand. Suppl. 1995, 386: 8-13), are potent monoamine oxidase inhibitors inducing irreversible inhibition of the respective enzymes. The (R)-isomer of deprenyl (Selegilin®, compound (R)-A) is a more potent inhibitor than the (S)-isomer (not shown).

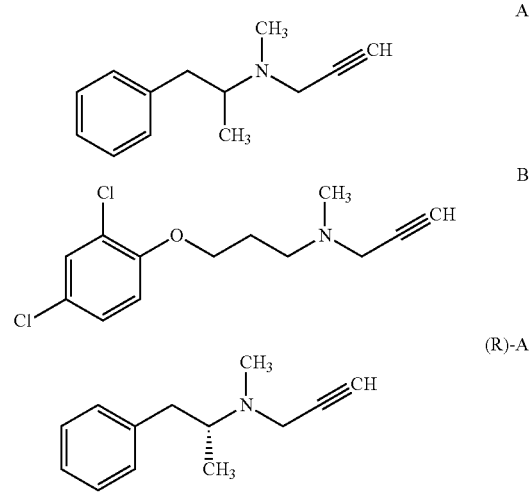

Neuroprotective and other pharmaceutical effects have also been described for inhibitors (Curr. Pharm. Des. 2010, 16: 2799-2817, Nature Reviews Neuroscience 2006, 295: 295-309; Br. J. Pharmacol. 2006, 147: 5287-5296, J. Alzheimers Dis. 2010, 21: 361-371, Prog. Neurobiol. 2010, 92: 330-344).

MAO-B inhibitors are for example used to increase DOPA levels in CNS (Progr. Drug Res. 1992, 38: 171-297) and they have been used in clinical trials for the treatment of Alzheimer's disease (AD) based on the fact that an increased level of MAO-B is involved in astrocytes associated with Alzheimer plaques (Neuroscience 1994, 62: 15-30).

Fluorinated MAO inhibitors have been synthesised and biochemically evaluated (Kirk et al., Fluorine and Health, A. Tressaud and G. Haufe (editors), Elsevier 2008, pp. 662-699). $^{18}$F and $^{11}$C labelled MAO inhibitors have been studied in vivo (Journal of the Neurological Science 2007, 255: 17-22; review: Methods 2002, 27: 263-277).

$^{18}$F labelled deprenyl and deprenyl analogues (D) and (E) have also been reported (Int. J. Radiat. Appl. Instrument. Part A, Applied Radiation Isotopes, 1991, 42: 121; J. Med. Chem. 1990, 33: 2015-2019 and Nucl. Med. Biol. 1990, 26: 111-116, respectively).

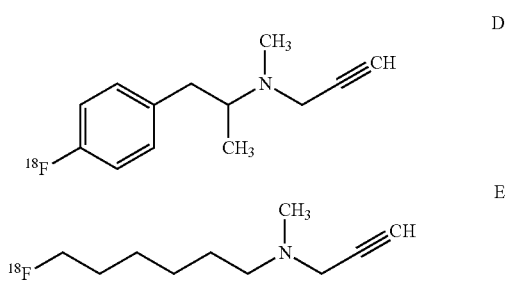

Amongst said $^{11}$C labelled MAO inhibitors, [$^{11}$C]-L-Deprenyl-D2, also referred to as DED ([$^{11}$C]-L-bis-deuterium-deprenyl), has been widely used by multiple groups to study CNS diseases with regard to their impact on MAO-B activity, such as epilepsy (Acta Neurol. Scand. 2001, 103: 360; Acta Neurol. Scand. 1998, 98: 224; Epilepsia 1995, 36: 712), amyotrophic lateral sclerosis (ALS, see J. Neurolog. Sci. 2007, 255: 17), and traumatic brain injury (Clin. Positron Imaging 1999, 2: 71).

deuterated counterpart (see e.g. J. Nucl. Med. 1995, 36: 1255; J. Neurochem. 1988, 51: 1524).

WO 2009/052970 A2 discloses novel $^{18}$F labelled analogues of L-Deprenyl. Compound F shown below features favourable uptake in baboon brain and improved properties, such as superior metabolic stability, as compared to [$^{11}$C]-L-Deprenyl and the aforementioned $^{18}$F labelled MAO-B inhibitors D and E. It can be anticipated that deuteration at the propargylic position, as introduced in DED, will also result in a reduction of the trapping rate of compound F (Fowler et al. J. Neurochem. 1988; 51: 1524-1534).

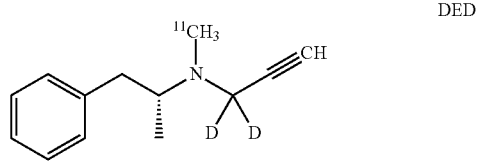 [SMILES: [2H]C([2H])(C#C)N([11CH3])[C@H](C)Cc1ccccc1]

DED

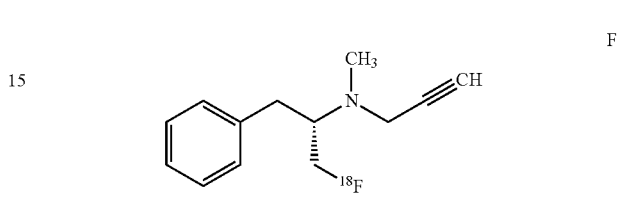

F

Moreover, a comparative multitracer study including DED has been performed in patients suffering from Alzheimer's disease (AD) and healthy controls (NeuroImage 2006, 33: 588).

DED has been furthermore used in studies on the effect of smoking and age on MAO-B activity (Neurobiol. Aging 1997, 18: 431; Nucl. Med. Biol. 2005, 32: 521; Proc. Nat. Acad. Sci. USA 2003, 20: 11600; Life Sci. 1998, 63: 2, PL19; J. Addict. Disease 1998, 17: 23).

The non-deuterated analogue of DED, [$^{11}$C]-L-deprenyl, binds very rapidly and irreversibly to MAO-B. As a result, the tracer may be trapped at a rate similar to or higher than its delivery by plasma, rendering PET images of regions with high MAO-B levels and/or low blood flow representing perfusion rather than MAO-B activity. The binding of DED is slower due to a kinetic isotope effect and thus DED allows for a more accurate assessment of MAO-B activity as its non- For the sake of clarity, the reader is referred to the fact that the synthesis of F, alike the preparation of suitable precursors thereof such as J from alcoholic intermediates such as G is thought to proceed via a rearrangement reaction involving an aziridinium ion H. Said rearrangement may give rise to regioisomeric mixtures of products as exemplified here. Thus, the regioisomeric precursors J1 and J2, due to the leaving group qualities of their chloro groups, can be equilibrated under suitable conditions, whilst F can be readily separated from its secondary regioisomer and is stable towards equilibration. For additional information on the aziridinium ion rearrangement see e.g. P. Gmeiner et al., J. Org. Chem. 1994, 59: 6766. The aziridinium rearrangement proceeds in a stereospecific manner, as described in WO 2010/121719 A1 (see also the aforementioned publication and J. Cossy et al., Chem. Eur. J. 2009, 15: 1064).

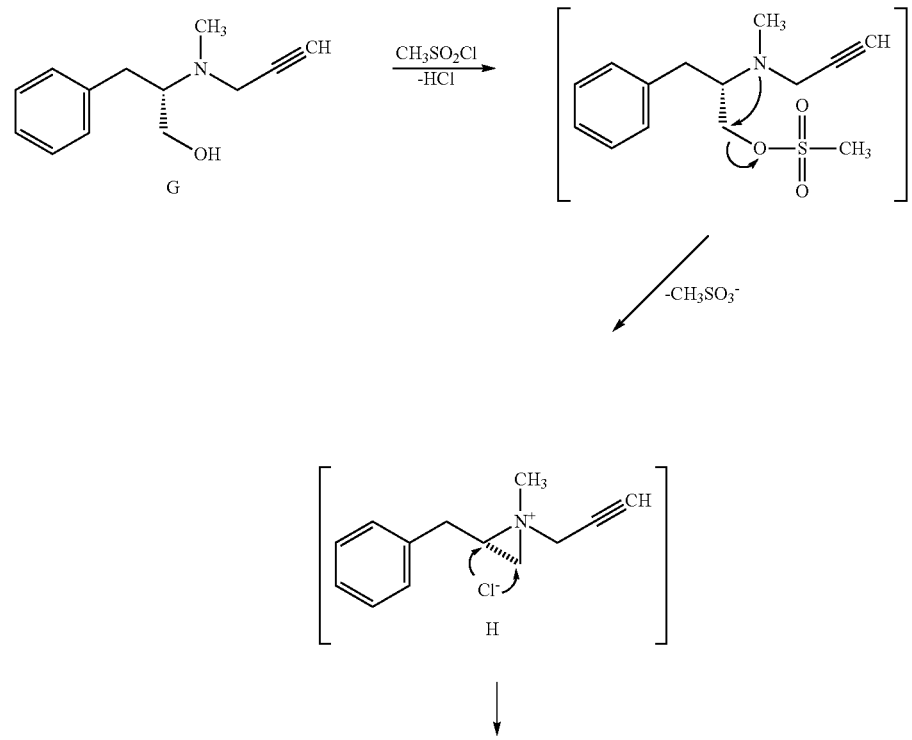

-continued

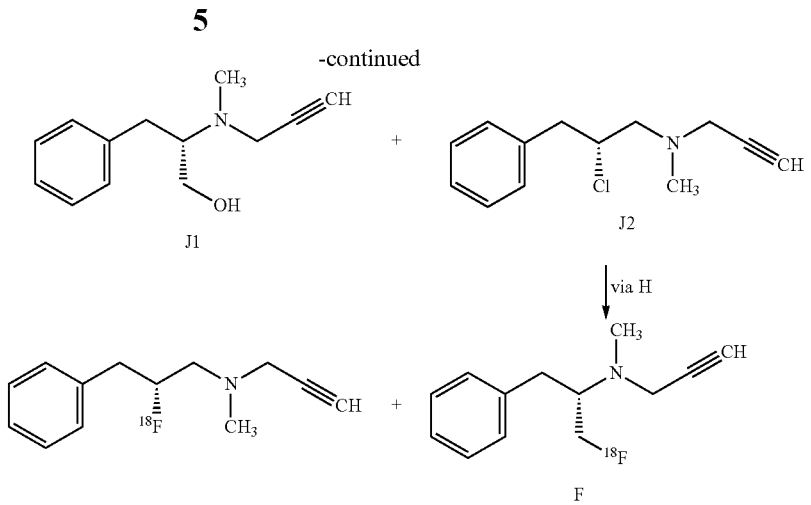

PROBLEM TO BE SOLVED AND ITS SOLUTION

The aim of the present invention was to find a $^{18}F$ labelled compound binding to MAO-B featuring superior signal to background ratio as compared to the current state of the art that can be used to detect reactive astrocytes by means of PET imaging targeting monoamine oxidase B, and to identify suitable precursors for its preparation.

This was achieved by the provision of the compounds of the current invention which showed excellent uptake in target regions which surprisingly was accompanied with a significantly enhanced washout resulting in lower undesired signals, such as non-specific binding, as highlighted in FIGS. 5a and 5b.

The effect strongly exceeds effects reported for compounds from the closest prior art (see literature references below) and hence could not be expected by the person skilled in the art.

Surprisingly, a decrease in signal intensity between 6-8 times from [$^{18}F$] Deprenyl towards [$^{18}F$] D2 Deprenyl was observed in the brain regions investigated during the steady state phase (see FIG. 5a).

From studies using [$^{11}C$] Deprenyl it is known that the MAO-B signal is underestimated in regions with high MAO-B activity due to high trapping rate that is similar to or exceeds delivery (Fowler et al. J Nucl Med 1995, 36: 1255). Deuteration of [$^{11}C$] Deprenyl has been reported to result in a reduced trapping rate leading to more reliable quantification of the signal. However, the effect of deuteration on the decrease in signal intensity for the [$^{11}C$] D2 Deprenyl (DED) observed in healthy baboon and human brain regions comparable to those investigated by us, e.g. striatum, thalamus, cortex, is only approximately 1.2-2.0 (Fowler et al. J. Neurochem 1988, 51: 1524-1534; J. Nucl. Med. 1995, 36: 1255-1262; Mol. Imaging. Biol. 2005, 7: 377-387). The unexpectedly pronounced improvement of aforementioned ratio (6 to 8 as compared to 1.2 to 2.0 in the prior art) renders the compounds of the invention as superior PET imaging agents.

SUMMARY OF THE INVENTION

The present invention covers compounds of general formula I

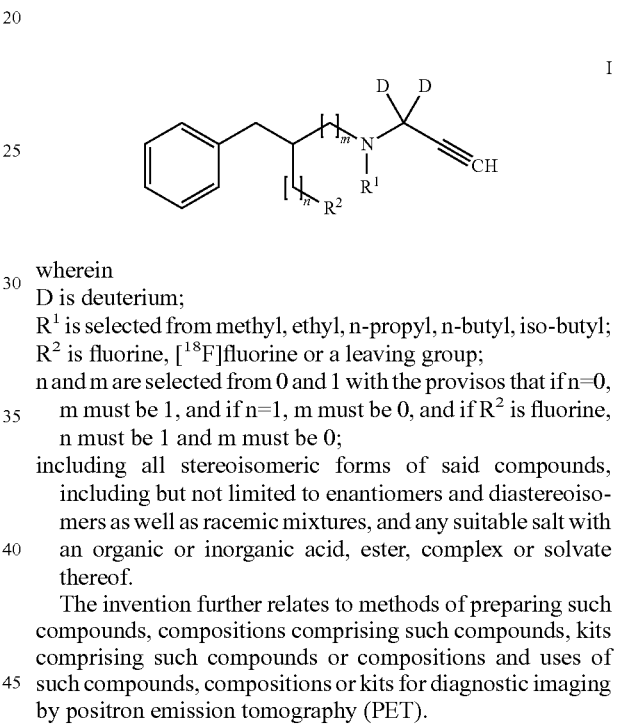

wherein
D is deuterium;
$R^1$ is selected from methyl, ethyl, n-propyl, n-butyl, iso-butyl;
$R^2$ is fluorine, [$^{18}F$]fluorine or a leaving group;
n and m are selected from 0 and 1 with the provisos that if n=0, m must be 1, and if n=1, m must be 0, and if $R^2$ is fluorine, n must be 1 and m must be 0;
including all stereoisomeric forms of said compounds, including but not limited to enantiomers and diastereoisomers as well as racemic mixtures, and any suitable salt with an organic or inorganic acid, ester, complex or solvate thereof.

The invention further relates to methods of preparing such compounds, compositions comprising such compounds, kits comprising such compounds or compositions and uses of such compounds, compositions or kits for diagnostic imaging by positron emission tomography (PET).

DETAILED DESCRIPTION OF THE INVENTION

Definitions

As used herein, a "leaving group" refers to a functional group selected from the group comprising halo, in particular chloro, bromo, iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

The term "aryl" as employed herein by itself or as part of another group refers to monocyclic or bicyclic aromatic groups containing from 6 to 12 carbons in the ring portion, preferably 6-10 carbons in the ring portion, such as phenyl, biphenyl, naphthyl or tetrahydronaphthyl. A preferred aryl group is phenyl.

As used herein in the description of the invention and in the claims, the term "alkyl", by itself or as part of another group, refers to a straight chain or branched chain alkyl group with 1 to 6 carbon atoms such as, for example methyl, ethyl, propyl, isopropyl, butyl, iso-butyl, tert-butyl, pentyl, iso-pentyl, neopentyl, hexyl.

As used herein in the description of the invention and in the claims, the terms "inorganic acid" and "organic acid", refer to mineral acids, including, but not being limited to: acids such as carbonic, nitric, phosphoric, hydrochloric, perchloric or sulfuric acid or the acidic salts thereof such as potassium hydrogen sulfate, or to appropriate organic acids which include, but are not limited to: acids such as aliphatic, cycloaliphatic, aromatic, araliphatic, heterocyclic, carboxylic and sulfonic acids, examples of which are formic, acetic, trifluoracetic, propionic, succinic, glycolic, gluconic, lactic, malic, fumaric, pyruvic, benzoic, anthranilic, mesylic, fumaric, salicylic, phenylacetic, mandelic, embonic, methansulfonic, ethanesulfonic, benzenesulfonic, phantothenic, toluenesulfonic, trifluormethansulfonic and sulfanilic acid, respectively.

The compounds of the present invention can exist as solvates, such as hydrates, wherein compounds of the present invention may contain organic solvents or water as structural element of the crystal lattice of the compounds. The amount of said solvents may exist in a stoichiometric or unstoichiometric ratio. In case of stoichiometric solvates, e.g. hydrates, hemi-, (semi-), mono-, sesqui-, di-, tri-, tetra-, penta- etc. solvates or hydrates are possible.

Since at least one chiral centre is present in the compounds according to the present invention and another form of an isomeric centre may be present, all isomeric forms resulting from said isomeric centres, including enantiomers and diastereoisomers, are intended to be covered herein. Compounds containing a chiral centre may be used as racemic mixture or as an enantiomerically enriched mixture, or the racemic mixture may be separated using well-known techniques and a single enantiomer may be used.

The terms "halogen", or "halo" refers to fluorine (F), chlorine (Cl), bromine (Br), or iodine (I); the term "halide" refers to fluoride, chloride, bromide or iodide.

SUBJECT MATTER OF THE PRESENT INVENTION

In a first aspect the invention is directed towards compounds of the general formula I

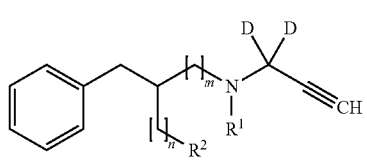

wherein
D is deuterium;
$R^1$ is selected from methyl, ethyl, n-propyl, n-butyl, iso-butyl;
$R^2$ is fluorine, [$^{18}$F]fluorine or a leaving group, wherein preferred leaving groups are selected from halogen, $C_1$-$C_6$-alkylsulfonyloxy, which is optionally substituted by fluorine, and arylsulfonyloxy, which is optionally substituted by hydrogen, methyl, halo and nitro, and wherein particularly preferred leaving groups are chloro, bromo, methanesulfonyloxy, and p-toluenesulfonyloxy, and wherein the most preferred leaving group is chloro;
n and m are selected from 0 and 1 with the provisos that if n=0, m must be 1, and if n=1, m must be 0, and if $R^2$ is fluorine, n must be 1 and m must be 0;
including all stereoisomeric forms of said compounds, including but not limited to enantiomers and diastereoisomers as well as racemic mixtures, and any suitable salt with an organic or inorganic acid, ester, complex or solvate thereof.

In a preferred embodiment, the invention is directed towards compounds of the general formula I:

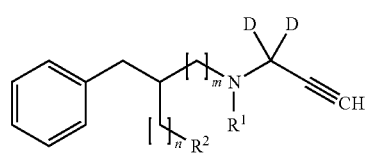

wherein
D is deuterium;
$R^1$ is methyl;
$R^2$ is selected from fluoro or chloro;
n and m are selected from 0 and 1 with the provisos that if n=0, m must be 1, and if n=1, m must be 0, and if $R^2$ is fluorine or [$^{18}$F]fluorine, n must be 1 and m must be 0;
including enantiomers as well as racemic mixtures, and any suitable salt with an organic or inorganic acid, or solvate thereof.

In a more preferred embodiment, the invention is directed towards a compound of the general formula Ia:

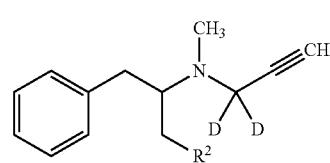

wherein
D is deuterium;
$R^2$ is selected from fluoro or chloro;
including enantiomers as well as racemic mixtures, and any suitable salt with an organic or inorganic acid, or solvate thereof.

In another more preferred embodiment, the invention is directed towards a compound of the general formula Ib:

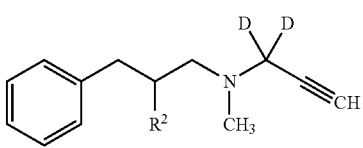

wherein
D is deuterium;
$R^2$ is chloro;
including enantiomers as well as racemic mixtures, and any suitable salt with an organic or inorganic acid, or solvate thereof.

In an even more preferred embodiment, the invention is directed towards the compound of the general formula Ic:

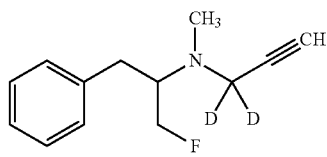

including enantiomers as well as racemic mixtures, and any suitable salt with an organic or inorganic acid, or solvate thereof.

In another even more preferred embodiment, the invention is directed towards a compound of the general formula Id:

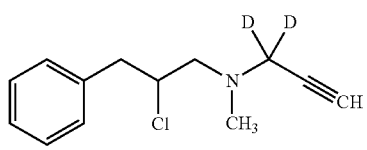

including enantiomers as well as racemic mixtures, and any suitable salt with an organic or inorganic acid, or solvate thereof.

In a particularly preferred embodiment, the invention is directed towards the compound of the general formula Ie:

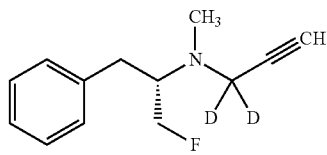

wherein $F={}^{18}F$;
and any suitable salt with an organic or inorganic acid, or solvate thereof.

In a particularly preferred embodiment, the invention is directed towards the compound of the general formula Ie:

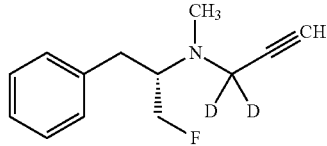

wherein $F={}^{19}F$,
and any suitable salt with an organic or inorganic acid, or solvate thereof.

In a particularly preferred embodiment, the invention is directed towards the compound of the general formula If:

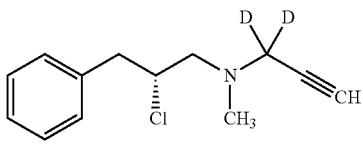

and any suitable salt with an organic or inorganic acid, or solvate thereof.

In a second aspect the invention is directed to the synthesis of a compound of the formula I, in which $R^2$ stands for a leaving group as defined above, from suitable starting materials. Such compounds are useful precursors for the introduction of $R^2={}^{18}F$, i.e. for the generation of ${}^{18}F$ labelled radiotracers. Said starting materials can comprise but are not limited to alcohols of the general formula IIa:

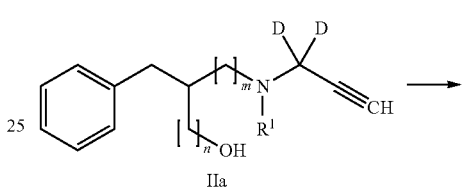

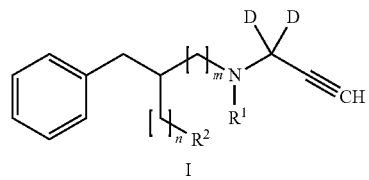

Such syntheses comprise but are not limited to the reaction with a sulfonyl halide, such as methanesulfonyl chloride or p-toluenesulfonyl chloride, in the presence of a suitable base, such as a trialkyl amine, e.g. triethylamine, or such as a heteroaromatic base, e.g. pyridine or 2,6-lutidine, in a suitable solvent such as an optionally halogenated hydrocarbon, e.g. dichloromethane, or an ether, such as tetrahydrofurane.

Said synthetic methods may further comprise, but are not limited to the use of sulfonyl anhydrides instead of the aforementioned sulfonyl halides, such as methanesulfonic anhydride, to give compound of the formula II in which $R^2$ is a sulfonic ester. Said synthetic methods may furthermore comprise the use of carbon tetrahalides, such as tetrachloromethane or tetrabromomethane, and suitable organophosphorus reagents such as triphenylphosphane or tri-n-butylphosphane, for the conversion of alcohols of the general formula IIa into compounds of the general formula I in which $R^2$ stands for a leaving group.

In a preferred embodiment, the invention is directed to a synthesis of the compound with formula Id as described above from the alcohol with the formula IIb:

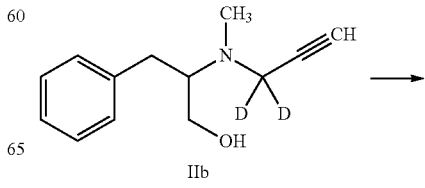

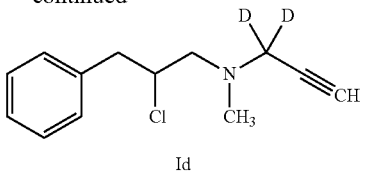

Id

In a more preferred embodiment, the invention is directed to a synthesis of the compound with formula Id as described above from the alcohol with the formula IIb by reacting IIb with a suitable sulfonyl chloride in the presence of a suitable base in an appropriate solvent, as described above.

In a particularly preferred embodiment, the invention is directed to a synthesis of the compound with formula If as described above from the alcohol with the formula IIc by reacting IIc with a suitable sulfonyl chloride in the presence of a suitable base in an appropriate solvent, as described above:

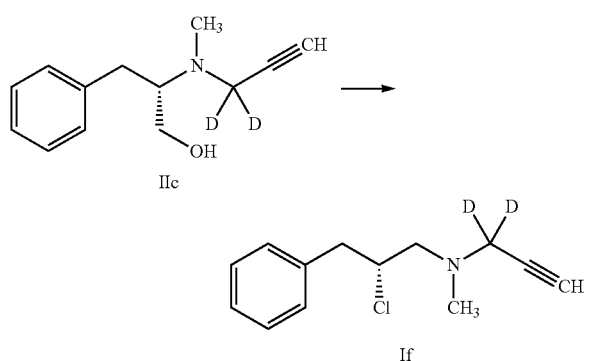

In another particularly preferred embodiment, the invention is directed to a synthesis of the compounds with formula Id or If as described above from alcohols with the formula IIb or IIc by reacting said alcohols with a sulfonyl chloride, such as methanesulfonyl chloride or p-toluenesulfonyl chloride, in the presence of a suitable base, such as a trialkyl amine, e.g. triethylamine, in a suitable solvent such as a halogenated hydrocarbon, e.g. dichloromethane, to effect conversion of the hydroxy group displayed by compounds of the formulae Ia into a chloro group. The reaction mixture resulting from bringing together all reactants is initially allowed to react for a suitable time ranging from 5 min to 6 hours, preferred 15 min to 4 hours, even more preferred 30 min to 2 hours, at a temperature between −50° C. and +30° C., preferred −30° C. and +30° C., even more preferred −10° C. and +25° C., followed by heating the reaction mixture for a suitable time ranging from 5 min to 6 hours, preferred 15 min to 4 hours, even more preferred 30 min to 2 hours to a temperature range between 70° C. to 130° C., preferred 80° C. to 120° C., even more preferred 90° C. to 110° C. The heating period effects the conversion of an initially formed mixtures of Id/If with their respective primary regioisomers reflecting the constitution of the respective starting material IIb or IIc.

In a third aspect the invention is directed towards a method of synthesis comprising the reaction of a compound of the general formula I, wherein $R^2$ stands for a leaving group, with an F-fluorinating agent, in which $F=^{18}F$, to give a compound in which $R^2$ is replaced by $^{18}F$. Said F-fluorinating agent is a compound comprising F-anions, preferably a compound selected from but not limited to the group comprising 4, 7, 13, 16, 21, 24-hexaoxa-1,10-diazabicyclo[8.8.8]-hexacosane K F, i.e. crown ether salt Kryptofix KF, KF, HF, KH F$_2$, CsF, NaF and tetraalkylammonium salts of F, such as tetrabutylammonium fluoride, and wherein $F=^{18}F$, to give a compound in which $R^2$ is replaced by $^{18}F$.

In a preferred embodiment, the invention is directed towards a method of synthesis of compound of the general formula Ic, in which $F=^{18}F$, by reacting compound of the general formula Id with an F-fluorinating agent, in which $F=^{18}F$. Said F-fluorinating agent is a compound comprising F-anions, preferably a compound selected from but not limited to the group comprising 4, 7, 13, 16, 21, 24-hexaoxa-1,10-diazabicyclo[8.8.8]-hexacosane K F, i.e. crown ether salt Kryptofix KF, KF, HF, KH F$_2$, CsF. NaF and tetraalkylammonium salts of F, such as tetrabutylammonium fluoride, and wherein $F=^{18}F$.

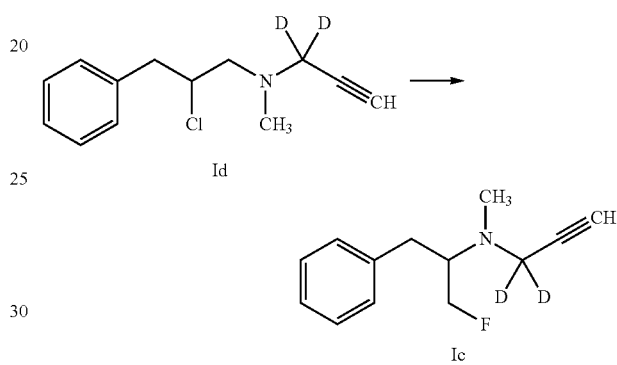

In another preferred embodiment, the invention is directed towards a method of synthesis of compound of the general formula Ie, in which $F=^{18}F$, by reacting compound of the general formula If with an F-fluorinating agent, in which $F=^{18}F$. Said F-fluorinating agent is a compound comprising F-anions, preferably a compound selected from but not limited to the group comprising 4, 7, 13, 16, 21, 24-hexaoxa-1, 10-diazabicyclo[8.8.8]-hexacosane K F, i.e. crown ether salt Kryptofix KF, KF, HF, KH F$_2$, CsF, NaF and tetraalkylammonium salts of F, such as tetrabutylammonium fluoride, and wherein $F=^{18}F$.

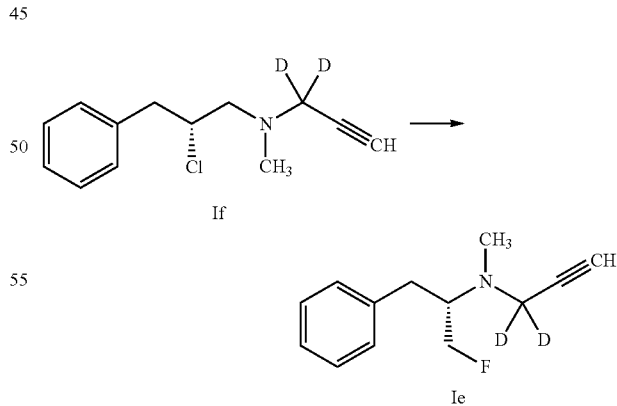

In a fourth aspect, the invention is directed towards the use of the compounds of the general formula I for the preparation of an $^{18}F$ labelled diagnostic imaging agent or imaging agent, preferably as imaging agent for PET application.

In a more preferred embodiment, said PET application is used for imaging of CNS diseases. CNS diseases include but are not limited to inflammatory and autoimmune, allergic, infectious and toxin-triggered and ischemia-triggered diseases, pharmacologically triggered inflammation with pathophysiological relevance, neuroinflammatory, neurodegenerative diseases.

More preferably, the CNS disease is selected from multiple sclerosis, Alzheimer's disease, frontotemporal dementia, dementia with Lewy bodies, leukoencephalopathy, epilepsy, neuropathic pain, amyotrophic lateral sclerosis, Parkinson's Disease, encephalopathies, brain tumors, depression, drug abuse, addictive diseases, atheroma, atherosclerosis, pharmacologically triggered inflammation, systemic inflammation of unclear origin.

In a particularly preferred embodiment, said PET application is used for imaging of dementia related diseases, such as Alzheimer's disease.

In another particularly preferred embodiment, said PET application is used for imaging neuroinflammatory diseases, such as multiple sclerosis.

The invention also relates to kits comprising compounds of formula I. Such kits may contain at least one sealed vial containing a compound of formula I. The kit may also contain reagents suitable to perform the herein disclosed reactions. The reagents disclosed herein may be also included in such kit and may be stored in a sealed vial. The kit may also contain $^{18}F$ labelling reagents. Furthermore, the kit may contain instructions for its use.

In a fifth aspect, the invention is directed to the use of compounds of general formula I, for conducting biological assays and chromatographic identification. More preferably, the use relates to compounds of general formula I wherein $R^2$ is $^{18}F$ or $^{19}F$. more preferably $^{19}F$.

Compounds of general formula I wherein the fluorine isotope is $^{19}F$ are useful as references and/or measurement agents.

The compounds of general formula I are herein defined as above and encompass all embodiments and preferred features.

In particular the invention relates to:
1. A compound of formula I:

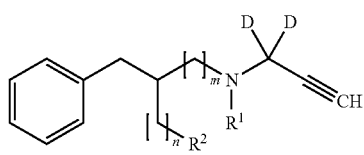

wherein
D is deuterium;
$R^1$ is selected from methyl, ethyl, n-propyl, n-butyl, iso-butyl;
$R^2$ is fluorine, [$^{18}F$]fluorine or a leaving group, wherein leaving groups are selected from halogen, $C_1$-$C_6$-alkylsulfonyloxy, which is optionally substituted by fluorine, and arylsulfonyloxy, which is optionally substituted by hydrogen, methyl, halo and nitro;
n and m are selected from 0 and 1 with the provisos that if n=0, m must be 1, and if n=1, m must be 0, and if $R^2$ is fluorine, n must be 1 and m must be 0;
including all stereoisomeric forms of said compounds, including but not limited to enantiomers and diastereoisomers as well as racemic mixtures, and any suitable salt with an organic or inorganic acid, ester, complex or solvate thereof.

2. A compound according to count 1,
wherein $R^2$ is selected from the group consisting of chloro, bromo, methanesulfonyloxy, and p-toluenesulfonyloxy.
3. A compound according to counts 1 or 2, wherein
D is deuterium;
$R^1$ is methyl;
$R^2$ is selected from fluoro or chloro.
4. A compound of formula Ia:

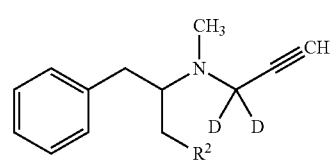

wherein
D is deuterium;
$R^2$ is selected from fluoro or chloro;
including enantiomers as well as racemic mixtures, and any suitable salt with an organic or inorganic acid, or solvate thereof.
5. A compound of formula Ib:

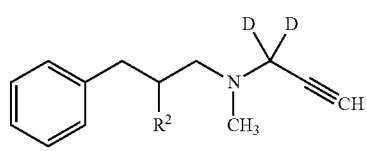

wherein
D is deuterium;
$R^2$ is chloro;
including enantiomers as well as racemic mixtures, and any suitable salt with an organic or inorganic acid, or solvate thereof.
6. A compound selected from the group of compounds consisting of a compound of formula Ic,

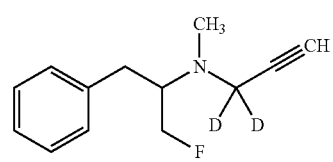

a compound of formula Id,

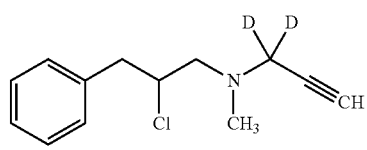

a compound of formula Ie,

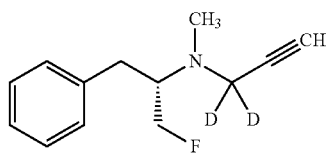

wherein F=$^{18}$F,
a compound of formula Ie,

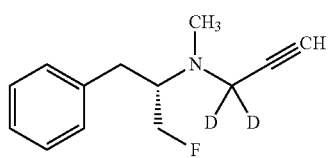

wherein F=$^{19}$F,
a compound of formula If,

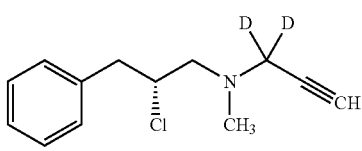

and any suitable salt with an organic or inorganic acid, or solvate thereof.

7. A [$^{18}$F] labelled compound of counts 1, 3, 4, and 6 as a diagnostic compound for PET imaging.

8. A diagnostic composition comprising a [$^{18}$F] labelled compound of counts 1, 3, 4, and 6 for PET imaging.

9. A [$^{18}$F] labelled compound of counts 1, 3, 4, and 6 as a diagnostic compound for PET imaging of CNS diseases.

10. A diagnostic composition comprising a [$^{18}$F] labelled compound of counts 1, 3, 4, and 6 for PET imaging of CNS diseases.

11. A compound or a composition according to count 7 to 10 for imaging of Alzheimer's disease.

12. A compound or a composition according to counts 7 to 11, wherein the [$^{18}$F] labelled compound is a compound of formula Ie:

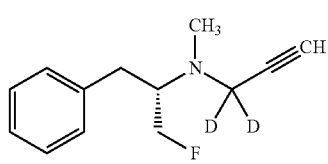

wherein F=$^{18}$F.

13. A method for the synthesis of a compound according to formula I:

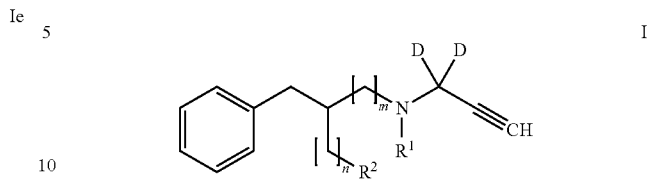

wherein
D is deuterium;
R$^1$ is selected from methyl, ethyl, n-propyl, n-butyl, iso-butyl;
R$^2$ is a leaving group, wherein leaving groups are selected from halogen, C$_1$-C$_6$-alkylsulfonyloxy, which is optionally substituted by fluorine, and arylsulfonyloxy, which is optionally substituted by hydrogen, methyl, halo and nitro;
n and m are selected from 0 and 1 with the provisos that if n=0, m must be 1, and if n=1, m must be 0, and if R$^2$ is fluorine, n must be 1 and m must be 0;
characterized in that
a compound of formula IIa:

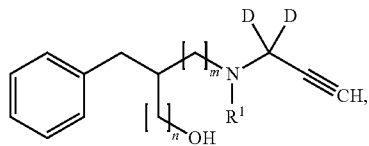

is reacted with a sulfonyl anhydride or a sulfonyl halide.

14. A method for the synthesis of a compound according to formula Ib:

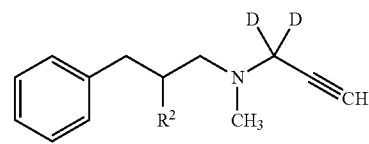

wherein
D is deuterium;
R$^2$ is chloro;
characterized in that
a compound of formula IIb:

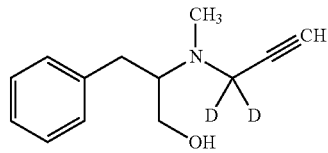

is reacted with a sulfonyl chloride.

15. A method according to count 14, wherein the sulfonyl chloride is methanesulfonyl chloride.

16. A method according to count 14 or 15, for the synthesis of a compound of formula If:

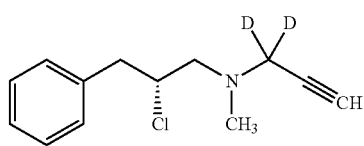

characterized in that
a compound of formula IIc:

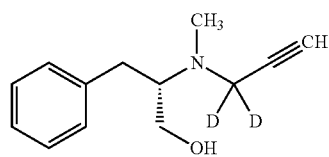

is reacted with methanesulfonyl chloride.

17. A method for the synthesis of a compound according to formula I:

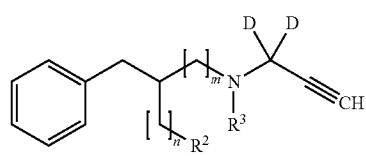

wherein
D is deuterium;
$R^1$ is selected from methyl, ethyl, n-propyl, n-butyl, iso-butyl;
$R^2$ is [$^{18}$F]fluorine;
n is 1 and m is 0;
characterized in that
a compound of formula I:

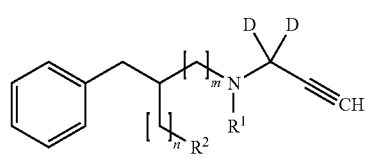

wherein
D is deuterium;
$R^1$ is selected from methyl, ethyl, n-propyl, n-butyl, iso-butyl;
$R^2$ is a leaving group, wherein leaving groups are selected from halogen, $C_1$-$C_6$-alkylsulfonyloxy, which is optionally substituted by fluorine, and arylsulfonyloxy, which is optionally substituted by hydrogen, methyl, halo and nitro;
n is 0 and m is 1;
is reacted with a suitable F-fluorinating agent, wherein F is $^{18}$F.

18. A method according to count 17 for the synthesis of a compound of formula Ic:

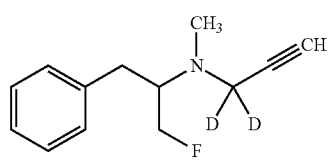

wherein F is $^{18}$F;
characterized in that
a compound of formula Id:

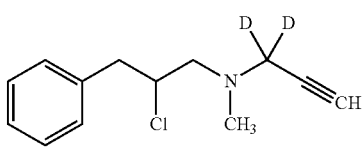

is reacted with a suitable F-fluorinating agent, wherein F is $^{18}$F.

19. A method according to count 17 or 18 for the synthesis of a compound of formula Ie:

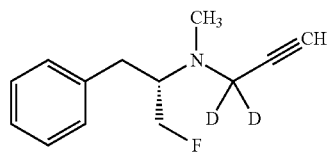

wherein F is $^{18}$F,
characterized in that
a compound of formula If:

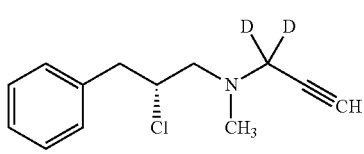

is reacted with a suitable F-fluorinating agent, wherein F is $^{18}$F.

20. A kit comprising at least one sealed container comprising a compound or a composition according to counts 1-12.
21. A kit comprising at least one sealed container comprising a compound of count 6.
22. A kit according to counts 20 and 21 comprising a further sealed container comprising reagents.
23. The use of a $^{18}$F-labelled compound of counts 1 to 6 in the preparation of a diagnostic composition for PET imaging of a CNS disease, wherein more preferably the CNS disease is Alzheimer's disease.
24. The use of a $^{18}$F-labelled compound of counts 1 to 6 in a PET method of diagnosing a CNS disease, more preferably Alzheimer's disease comprising administering said compound in a diagnostically effective amount to a patient.

25. The use of a F-labelled compound of counts 1 to 6 for conducting biological assays and chromatographic identification, wherein F is $^{18}$F or $^{19}$F.

In the context of this invention, CNS diseases include but are not limited to inflammatory and autoimmune, allergic, infectious and toxin-triggered and ischemia-triggered diseases, pharmacologically triggered inflammation with pathophysiological relevance, neuroinflammatory, neurodegenerative diseases. More preferably, the CNS disease is selected from multiple sclerosis, Alzheimer's disease, frontotemporal dementia, dementia with Lewy bodies, leukoencephalopathy, epilepsy, neuropathic pain, amyotrophic lateral sclerosis, Parkinson's Disease, encephalopathies, brain tumors, depression, drug abuse, addictive diseases, atheroma, atherosclerosis, pharmacologically triggered inflammation, systemic inflammation of unclear origin.

In a particularly preferred embodiment, said PET application is used for imaging of dementia related diseases, such as Alzheimer's disease.

In another particularly preferred embodiment, said PET application is used for imaging neuroinflammatory diseases, such as multiple sclerosis.

According to the invention, the $^{18}$F-labelled compounds of the invention are useful PET tracers for imaging of or diagnosing CNS diseases in particular for Alzheimer's disease and multiple sclerosis.

GENERAL SYNTHESIS OF COMPOUNDS OF THE INVENTION

The synthesis of the compounds of the invention commences with amino alcohol intermediates of the general formula II. Many of these amino alcohols are known to the person skilled in the art and readily synthesised from suitable amino acid building blocks or suitably protected intermediates which are often commercially available. Subsequently, the deuterated propargyl group is introduced to give tertiary amines IIa. This can be performed using crude 3-bromo(3,3-$^2$H$_2$)prop-1-yne prepared according to Fowler et al., Nucl. Med. Biol. 2001, 28 (7): 779-785; in our hands however, the corresponding tosylate III was found to be more practical due to its lower volatility and better detectability. It is easily prepared from the deuterated propargyl alcohol described in the reference given above.

Scheme 1: Preparation of intermediates of the general formula IIa from starting materials of the general formula II, wherein R$^1$, n and m are defined as the claims and description of this invention.

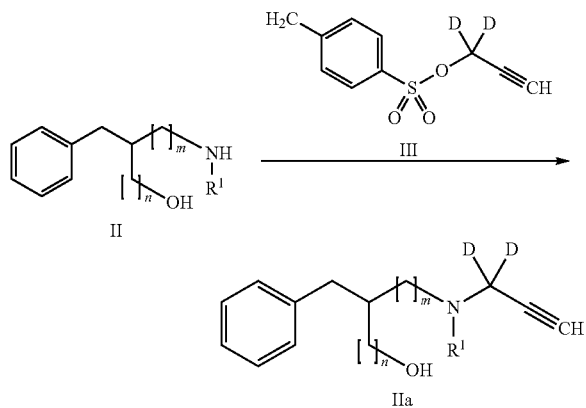

The hydroxy group of the resulting amino alcohol IIa is then transferred into a leaving group by methods known to the person skilled in the art, such as sulfonylation or halogenation.

Scheme 2: Preparation of compounds of the invention of the general formula I, wherein R$^1$, n and m are defined as in the claims and description of this invention, and wherein R$^2$ is a leaving group, from intermediates of the general formula IIa, wherein R$^1$, n and m are defined as in the claims and description of this invention.

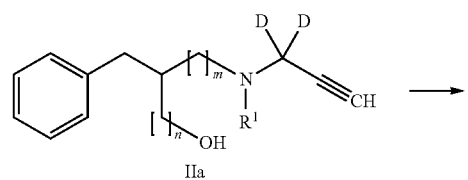

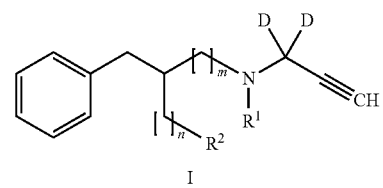

It is worth noting at this point that sulfonates are only available from sulfonyl anhydrides since the sulfonates initially formed from sulfonyl chlorides get readily displaced by the concomitant chloride counterion. Said sulfonates have been reported to readily undergo a rearrangement via an intermediate aziridinium ion which may give rise to regiosiomeric mixtures of products, see e.g. L. Lehmann et al., WO 2009/052970 A2. For additional information on the aziridinium ion rearrangement see e.g. P. Gmeiner at al., J. Org. Chem. 1994, 59: 6766. The aziridinium rearrangement proceeds in a stereospecific manner, as described in WO 2010/121719 A1 (see also the aformentioned publication and J. Cossy et al., Chem. Eur. J. 2009, 15: 1064). Under suitable conditions conferring thermodynamic control, the thermodynamically more stable product can be formed with high selectivity as shown in the example shown below, as illustrated below for the synthesis of compound If.

Scheme 3: Preparation of compound of the invention of the general formula If via a rearrangement involving an aziridinium ion.

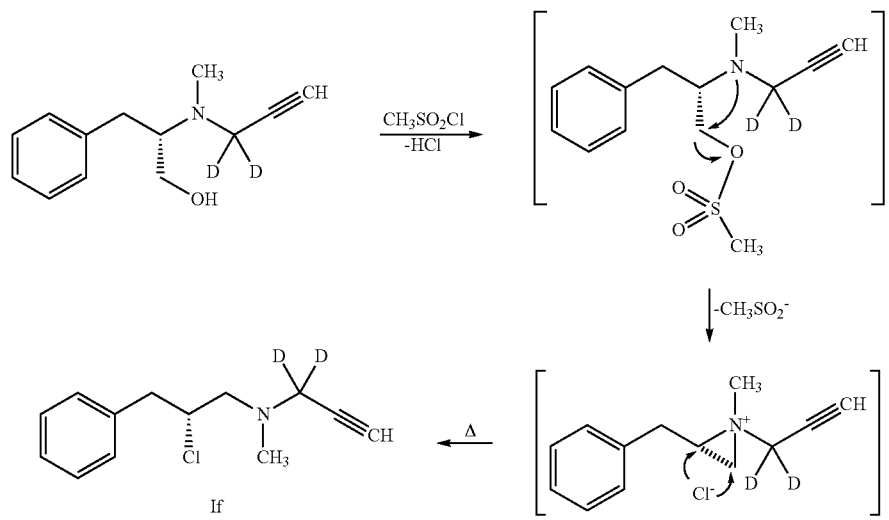

The resulting compounds with the general formula I wherein R² is a leaving group can be converted into ratiotracers (wherein R²=¹⁸F) by radiofluorination methods known to the person skilled in the art, e.g. 4, 7, 13, 16, 21, 24-hexaoxa-1,10-diazabicyclo[8.8.8]-hexacosane K F. i.e. crown ether salt Kryptofix KF, KF, HF, KH F₂, CsF, NaF and tetraalkylammonium salts of F, such as tetrabutylammonium fluoride, and wherein F=¹⁸F, Also these reactions typically yield regioisomeric mixtures, presumably via an intermediate aziridinium ion, which can be separated by means of HPLC to give the desired primary regioisomers Ig.

Scheme 4: Preparation of compounds of the invention of the general formula Ig, wherein R¹ is defined as in the claims and description of this invention, from compounds of the invention of the general formula I, wherein wherein R¹, n and m are defined as in the claims and description of this invention, and wherein R² is a leaving group.

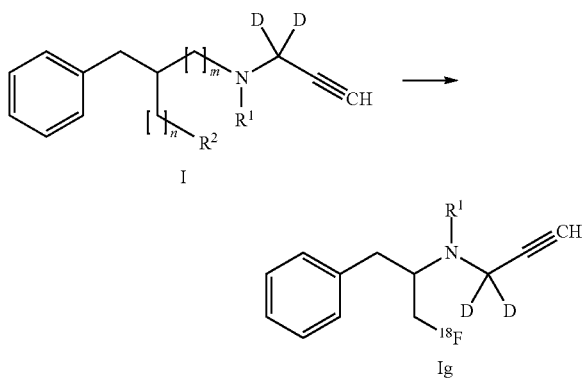

In a similar fashion, the amino alcohols IIa can be converted into the corresponding non-radioactive fluorides Ih by methods known to the person skilled in the art, such as the reaction with nonafluorobutylsulfonyl fluoride in the presence of Et₃N×3 HF. Also these reactions typically yield regioisomeric mixtures, presumably via an intermediate aziridinium ion.

Scheme 5: Preparation of compounds of the invention of the general formula Ih, wherein R¹ is defined as in the claims and description of this invention, from intermediates of the general formula IIa, wherein wherein R¹, n and m are defined as in the claims and description of this invention.

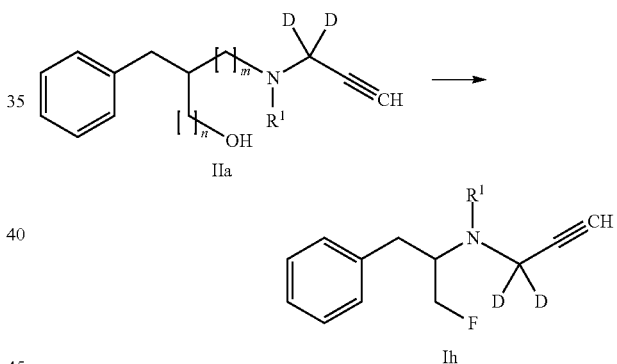

3-[$^{18}$F] Nordeprenyl and [$^{18}$F] D2 Nordeprenyl, resp.; 4-[$^{18}$F] D2 Deprenyl and non-deuterated [$^{18}$F] Deprenyl, respectively.

Figure 3:
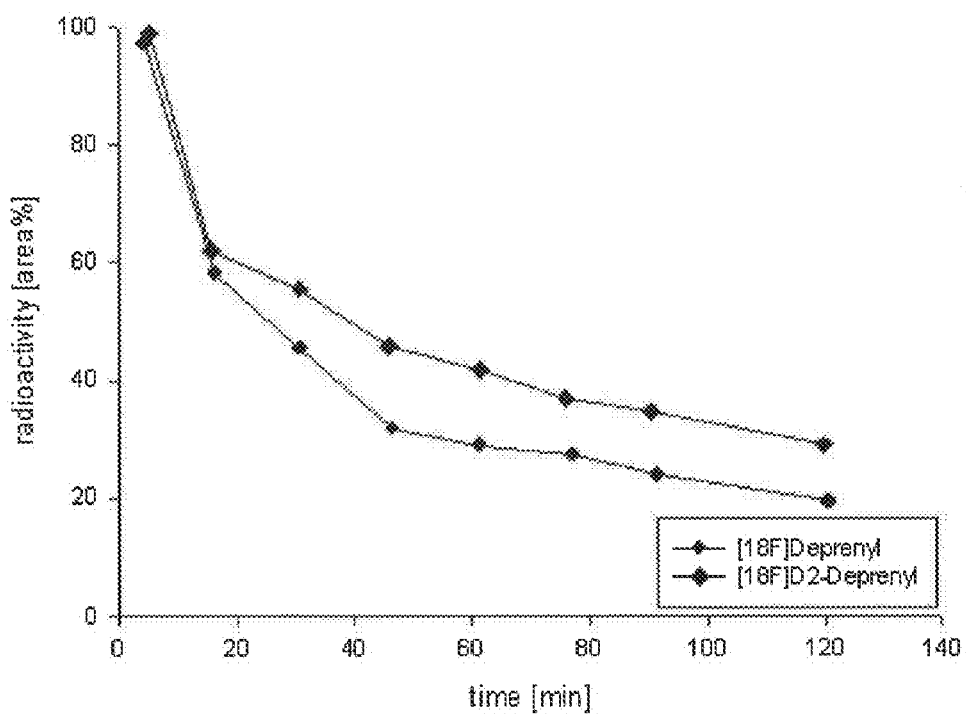

FIG. 3: Demonstration of in vivo time course of [$^{18}$F] D2 Deprenyl and non-deuterated [$^{18}$F] Deprenyl in cynomolgus monkey plasma.

Figure 4:
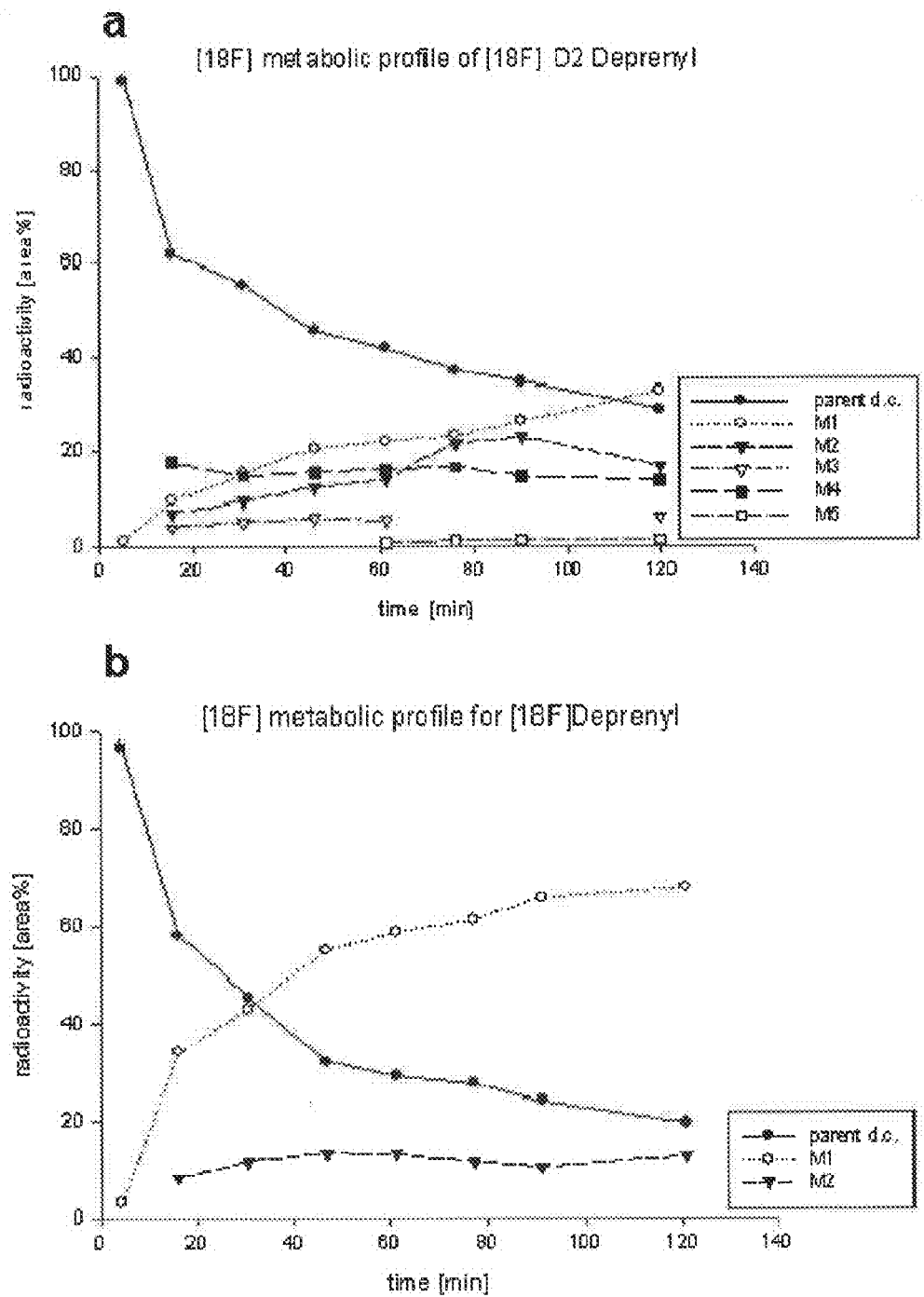

FIG. 4: Demonstration of in vivo metabolism of (a) [$^{18}$F] D2 Deprenyl and (b) non-deuterated [$^{18}$F] Deprenyl in cynomolgus monkey plasma. The time course of the parent compounds as well as metabolites expressed in [area %] generated from respective HPLC chromatograms are shown.

Figure 5:
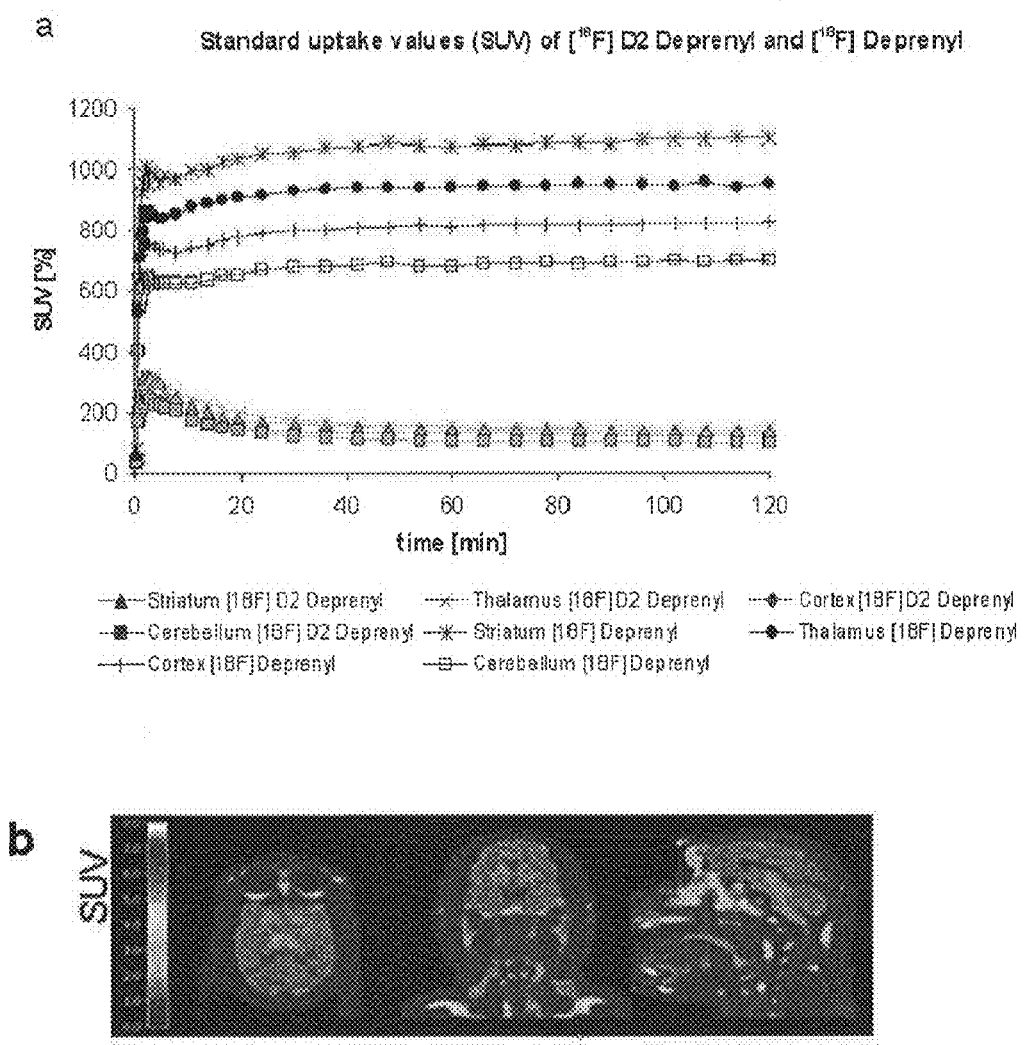

FIG. 5: PET in different brain regions of cynomolgus monkeys with [$^{18}$F] D2 Deprenyl and non-deuterated [$^{18}$F] Deprenyl, respectively. (a) Time activity curves (TAC) expressed as percent SUV of [$^{18}$F] D2 Deprenyl over a time of 120 min and compared to the respective TACs of non-deuterated [$^{18}$F] Deprenyl. (b) Images of three planes (transversal, coronal and sagittal) of the brain of the same cynomolgus monkey after the injection of [$^{18}$F] D2 Deprenyl.

Surprisingly, the decrease of the signal of [$^{18}$F] D2 Deprenyl, as expressed as % standard uptake value (SUV) in TACs compared to the signal of the non-deuterated [$^{18}$F] Deprenyl was 6 to 8 times between 30 and 120 min in the investigated brain regions of cynomolgus monkeys (FIG. 5a). This was not expected since the decrease in signal due to the deuteration effect known from [$^{11}$C] Deprenyl versus [$^{11}$C] D2 Deprenyl (DED) is only approximately 1.2-2.0 times observed in baboon and human brain regions comparable to those investigated by us, e.g. striatum, thalamus, cortex (Fowler et al. J. Neurochem 1988, 51: 1524-1534; J. Nucl. Med. 1995, 36: 1255-1262; Mol. Imaging. Biol. 2005, 7: 377-387).

Thus, the brain trapping also in target regions was less pronounced (FIG. 5b) and leads to an advantage over [$^{11}$C] D2 Deprenyl regarding background signal.

Figure 6:
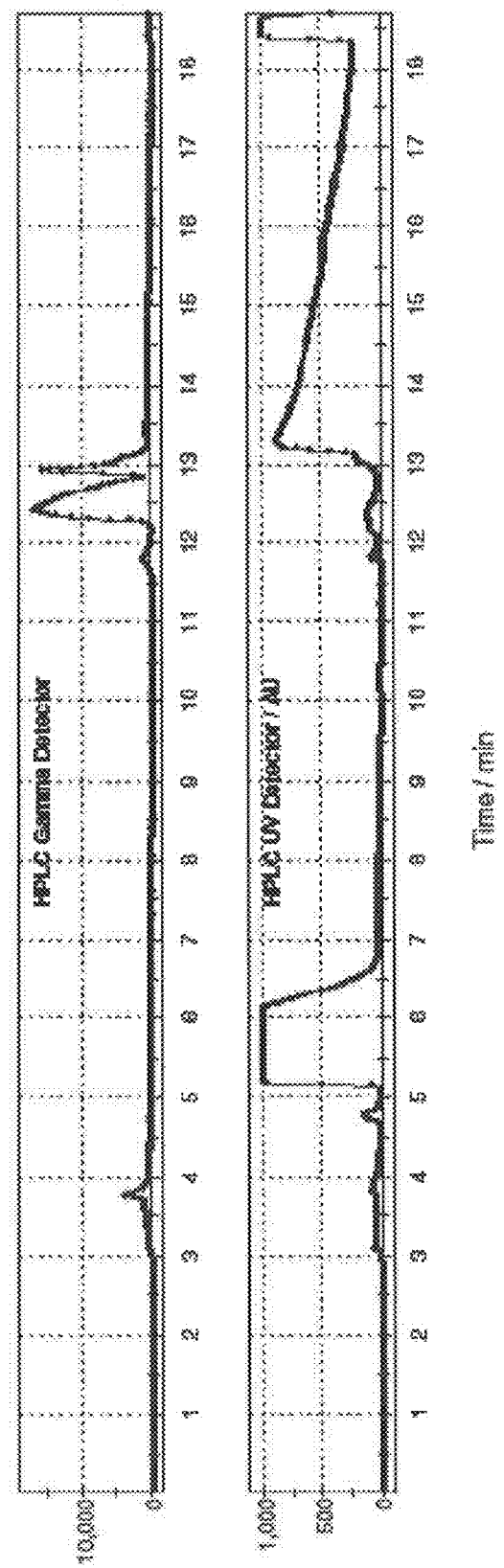

FIG. 6: Preparative HPLC chromatogram of [$^{18}$F] D2 Deprenyl showing a retention time of the desired $^{18}$F radiolabelled product of $t_R$=12.5 min.

Figure 7:
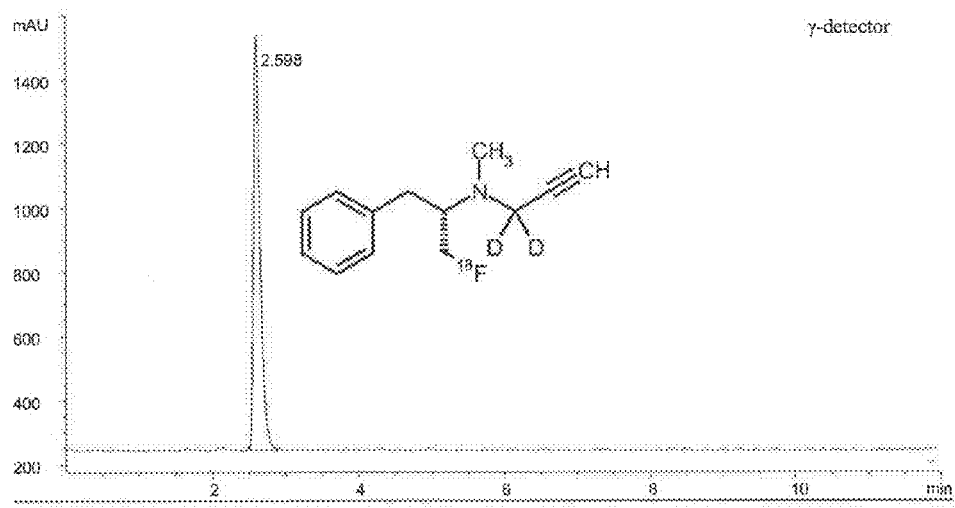

FIG. 7: Analytical HPLC chromatogram of [$^{18}$F] D2 Deprenyl showing a retention time of the desired $^{18}$F radiolabelled product of $t_R$=2.59 min.

Figure 8:
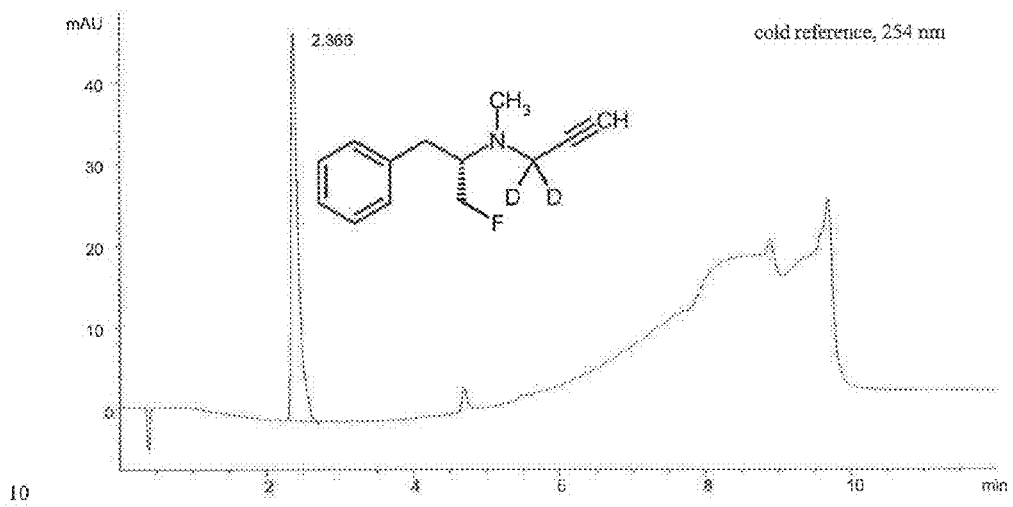

FIG. 8: Analytical HPLC chromatogram of [$^{19}$F] D2 Deprenyl (compound of Example 2) showing a retention time of the desired non-radioactive $^{19}$F reference compound of $t_R$=2.36 min.

FIG. 9: In vitro metabolite pathways in rat, mouse, dog, monkey and human microsomes and rat and human heaptocyte preparations. The metabolites were detected by LC/MS. (a) Metabolite pathways of non-deuterated [$^{18}$F] Deprenyl and (b) Metabolite pathways of [$^{18}$F] D2 Deprenyl.

Figure 10:
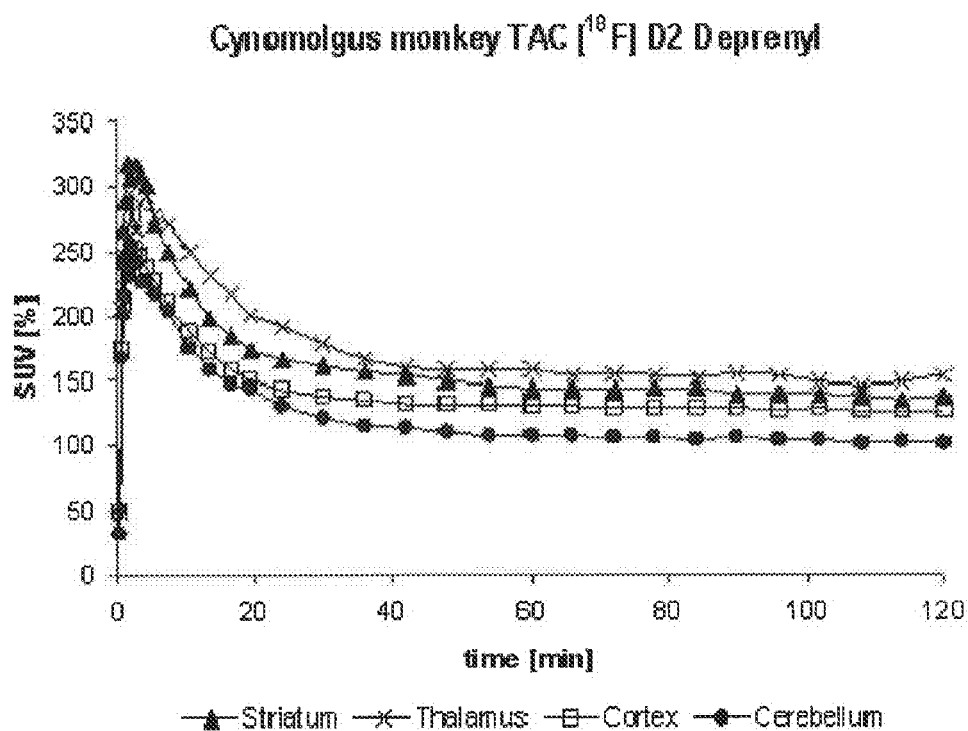

FIG. 10: Distribution of [$^{18}$F] D2 Deprenyl as observed by PET in different regions of a cynomolgus monkey brain. Time activity curves (TAC) were expressed as percent standard uptake values (SUV [%]) over a time of 120 min.

EXPERIMENTAL SECTION

General: All solvents and chemicals were obtained from commercial sources and used without further purification. The following table lists the abbreviations used in this paragraph and in the Examples section as far as they are not explained within the text body. NMR peak forms are stated as they appear in the spectra, possible higher order effects have not been considered. Chemical names were generated using the ACD IUPAC naming software by Advanced Chemical Development. In some cases generally accepted names of commercially available reagents were used in place of ACD/IUPAC generated names.

Reactions employing microwave irradiation can be run with a Biotage Initator® microwave optionally oven equipped with a robotic unit. The compounds and intermediates produced according to the methods of the invention may require purification. Purification of organic compounds is well known to the person skilled in the art and there may be several ways of purifying the same compound. In some cases, no purification may be necessary. In certain cases, the compounds may be purified by crystallization. In some cases, impurities may be removed by trituration using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with e.g. a FlashMaster II autopurifier (Argonaut/Biotage) and eluents such as gradients of hexane/EtOAc or dichloromethane/ethanol. In some cases, the compounds may be purified by preparative HPLC using for example a Waters autopurifier equipped with a diode array detector and/or online electrospray ionization mass spectrometer in combination with a suitable prepacked reverse phase column and eluents such as gradients of water and acetonitrile which may contain additives such as trifluoroacetic acid or aqueous ammonia. In some cases, purification methods as described above can provide those compounds of the present invention which possess a sufficiently basic functionality in the form of a salt, such as, in the case of a compound of the present invention which is sufficiently basic, a trifluoroacetate or formate salt for example. A salt of this type may be transformed into its free base form, respectively, by various methods known to the person skilled in the art.

| Abbreviations | |
|---|---|
| br | broad signal (in NMR) |
| d | doublet |
| dd | doublet of doublet |
| DMSO | dimethylsulfoxide |
| ee | enantiomeric excess |
| ESI | electrospray ionisation |
| EtOAc | ethyl acetate |
| Et$_2$O | diethyl ether |
| h | hour |
| K$_2$CO$_3$ | potassium carbonate |
| K$_{2.2.2}$ | 4, 7, 13, 16, 21, 24-hexaoxa-1,10-diazabioyclo[8.8.8]-hexacosane |
| MeCN | acetonitrile |
| MS | mass spectrometry |
| MTB | methyl tert-butyl ether |
| m | multiplet |
| min | minute |
| NMR | nuclear magnetic resonance spectroscopy: chemical shifts (δ) are given in ppm. |
| r.t. | room temperature |
| s | singlet |
| t | triplet |
| THF | tetrahydrofurane |

Intermediate 1A (2S)-2-(methylamino)-3-phenylpropan-1-ol

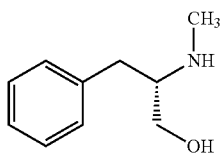

To a suspension of N-methyl-L-phenylalanine (20 g, 112 mmol) in THF (1200 mL) cooled to −10° C. was added in small portions lithium aluminium hydride (6.35 g, 167 mmol). After ceasing of the initial exothermic reaction, the cooling bath was removed and the reaction mixture was heated at reflux overnight. Subsequently, another portion of lithium aluminium hydride (4.24 g, 112 mmol) was added after cooling to −10° C., followed by refluxing for an additional 3 h. The reaction mixture was cooled to −40° C., and aqueous 2 N sodium hydroxide was added cautiously. After warming up to r.t., the mixture was filtered, the residue was washed with MTB, and the filtrate was evaporated to give the crude target compound (17.7 g, 96% yield) which was used without further purification.

$^1$H NMR (400 MHz, DMSO-$d_6$) δ ppm 2.26 (s, 3 H), 2.51-2.62 (m, 3 H) 3.16-3.30 (m, 3 H), 7.11-7.25 (m, 5 H).

MS (ESI): [M+H]$^+$=166.

Intermediate 1B (1,1-$^2$H$_2$)prop-2-yn-1-yl 4-methylbenzenesulfonate

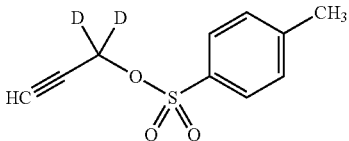 [SMILES: [2H]C([2H])(C#C)OS(=O)(=O)c1ccc(C)cc1]

To a solution of (1,1-$^2$H$_2$)prop-2-yn-1-ol (3.40 g, prepared according to Fowler et al., Nucl. Med. Biol. 2001, 28 (7): 779-785, separation from residual ethanol was accomplished by fractional distillation) in dichloromethane (250 mL) was added pyridine (7 mL), and the mixture was cooled to 0° C. Tosyl anhydride (21.0 g, 1.1 eq) was added and the reaction mixture was allowed to stir for 30 min, the cooling bath was removed and stirring was continued for 1.5 h. The mixture was concentrated in vacuo and the residue was purified by column chromatography on silica gel (EtOAc in hexane 2.5%→25%) to give the target compound in approx. 90% purity (9.39 g, 68% yield).

$^1$H NMR (300 MHz, CDCl$_3$) δ ppm 2.47 (m app s, 4 H), 7.36 (d, 2 H), 7.83 (d, 2 H).

MS (ESI): [M+H]$^+$=213.

Intermediate 1C (2S)-2-{methyl[(1,1-$^2$H$_2$)prop-2-yn-1-yl]amino}-3-phenyl-propan-1-ol

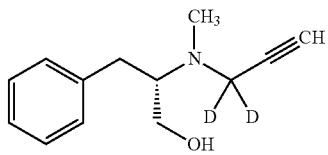 [SMILES: [2H]C([2H])(C#C)N(C)[C@H](CO)Cc1ccccc1]

To a solution of (2S)-2-(methylamino)-3-phenylpropan-1-ol (3.00 g, 18.2 mmol) in THF (150 mL) was added potassium carbonate (325 mesh, 3.76 g, 1.50 eq) at r.t. Intermediate 1B was added, and the mixture was stirred overnight at r.t. In order to effect complete turnover, another portion of potassium carbonate (0.50 eq) was added, and the mixture was stirred at r.t. for additional 2 h. The mixture was a concentrated in vacuo and partitioned between dichloromethane and brine. The organic layer was dried over sodium sulfate and evaporated. The residue was purified by column chromatography on silica gel (EtOAc in hexane 9%→90%) to give the desired product (2.07 g, 50% yield).

$^1$H NMR (600 MHz, CHLOROFORM-d) δ ppm 2.29 (s, 1 H) 2.37-2.43 (m, 1 H) 2.44 (s, 3 H) 2.75-2.95 (s br, 1 H) 3.05-3.12 (m, 2 H) 3.33-3.39 (m, 1 H) 3.41-3.46 (m, 1 H) 7.16-7.32 (m, 5 H).

MS (ESI): [M+H]$^+$=206.

Example 1

N-[(2R)-2-chloro-3-phenylpropyl]-N-methyl(1,1-$^2$H$_2$)prop-2-yn-1-amine

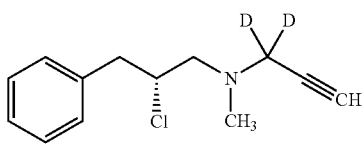 [SMILES: [2H]C([2H])(C#C)N(C)C[C@H](Cl)Cc1ccccc1]

To a solution of (2S)-2-{methyl[(1,1-$^2$H$_2$)prop-2-yn-1-yl]amino}-3-phenylpropan-1-ol (57 mg, 0.28 mmol) in dichloromethane (3 mL) was added triethylamine (58 μL, 0.42 mmol), and the mixture was cooled to 0° C. Methanesulfonyl chloride (28 μL, 0.36 mmol) was added, and the cooling bath was removed. After stirring at r.t. for 1 h, the reaction mixture was heated to 100° C. in a microwave oven for 1 h. After cooling to r.t., the mixture was diluted with diethyl ether (3 mL) and then washed by aqueous sodium bicarbonate. The aqueous layers were extracted with diethylether (2×3 mL), and the combined organic layers were diluted with dichloromethane and finally washed with brine. The organic layer was dried over sodium sulfate and evaporated. Column chromatography on silica (Et$_2$O in pentane 5%→15%) gave the title compound containing only small quantities of the corresponding primary regioisomer (50 mg, 80% yield).

$^1$H NMR (400 MHz, CHLOROFORM-d) δ ppm 2.21 (s, 1 H) 2.38 (s, 3 H) 2.74 (d, 2 H) 2.95 (dd, 1 H) 3.23 (dd, 1 H) 4.10-4.19 (m, 1 H) 7.23-7.36 (m, 5 H).

MS (ESI): [M+H]$^+$=224.

Example 2

N-[(2S)-1-fluoro-3-phenylpropan-2-yl]-N-methyl(1, 1-$^2$H)prop-2-yn-1-amine

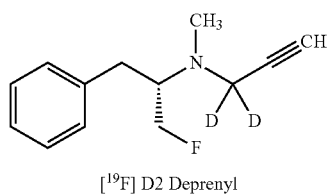 [SMILES: [2H]C([2H])(C#C)N(C)[C@H](CF)Cc1ccccc1]

[$^{19}$F] D2 Deprenyl

To a solution of (2S)-2-{methyl[(1,1-$^2$H$_2$)prop-2-yn-1-yl]amino}-3-phenylpropan-1-ol (2.00 g, 9.74 mmol) in THF (50 mL) was added subsequently nonafluorobutanesulfonyl fluoride (5.89 g, 2.0 eq), triethylamine tris-hydrofluoride (3.14 g, 2.0 eq), and triethylamine (8.15 mL, 6.0 eq), and the resulting mixture was stirred for 24 h at r.t. After concentration in vacuo, the crude residue was purified by column chromatography on silica (5%→15% EtOAc in hexane) to give the pure title compound as an oil (220 mg, 10% yield).

In addition, the regioisomer N-[(2R)-2-fluoro-3-phenylpropyl]-N-methyl(1,1-$^2$H$_2$)prop-2-yn-1-amine (380 mg, 19% yield), and a mixed fraction composed from both regioisomers (400 mg, 20%) was obtained.

Example 3

N-[(2S)-1-[$^{18}$F]fluoro-3-phenylpropan-2-yl]-N-methyl(1,1-$^2$H$_2$)— prop-2-yn-1-amine

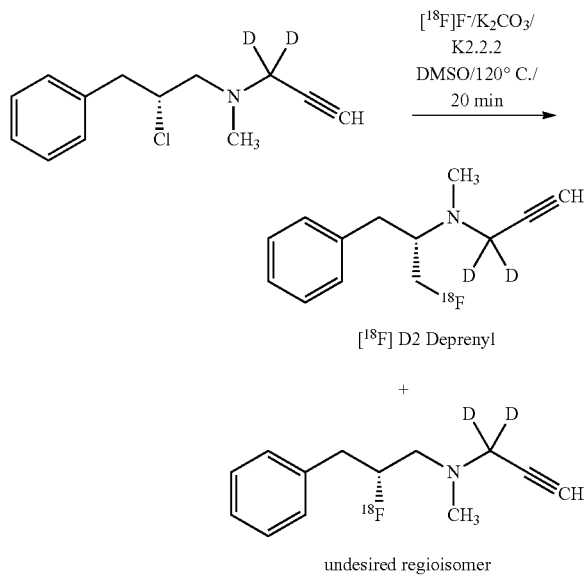

A solution of [$^{18}$F]fluoride in [$^{18}$O] enriched water was flashed through a Sep-Pak QMA light cartridge (preconditioned with potassium carbonate [0.5 M, 5 mL], 18 MΩ H$_2$O, 10 mL) to isolate 15 GBq of [$^{18}$F]fluoride which was then eluted from the cartridge with .1.5 mL of a solution of potassium carbonate and Kryptofix 2.2.2 in water and acetonitrile (5 mg K$_{222}$ in 0.95 mL MeCN, 1 mg K$_2$CO$_3$ in 0.05 mL water). The solvent was evaporated at 120° C. under continuous nitrogen flow and a yellow residue of [$^{18}$F]F$^-$/K$_2$CO$_3$/K2.2.2 was left. 1 mL of extra dry acetonitrile was added and evaporated as before. The residue was then cooled to 50° C. and N-[(2R)-2-chloro-3-phenylpropyl]-N-methyl(1,1-$^2$H$_2$) prop-2-yn-1-amine (Example 2; ~2 mg) dissolved in DMSO (600 µL) was added. The dosed reaction vessel was heated at 120° C. for 20 min. The reaction mixture was cooled to 50° C. and was diluted with 4 mL of the mobile phase before injecting to the preparative HPLC for purification.

The desired primary regioisomer N-[(2S)-1-[$^{18}$F]fluoro-3-phenylpropan-2-yl]-N-methyl(1,1-$^2$H$_2$)prop-2-yn-1-amine was purified by reverse phase HPLC on a ACE 5 C18 HL 250×10 mm; 5 µm and 85% 0.01 M H$_3$PO$_4$/15% MeCN was used as the eluting solvent at a flow rate of 4 mL/min. The eluate was monitored by a UV absorbance detector (λ=254 nm) in series with a radioactivity detector. The fraction of the desired compound was collected at t$_R$=12.5 min (FIG. 6) and diluted with 40 mL water. The dissolved product was transferred to a Sep-Pak C18 plus cartridge. The cartridge was washed with 5 mL of water and the desired $^{18}$F labelled product was eluted with 1 mL ethanol into the product vial (2.77 GBq). The radiochemical purity of the radioligand was analyzed by a reverse phase HPLC on a ACE 3 C18 S/N—A67537; 50×4.6 mm; 3 µm. with a solvent gradient: start 5% acetonitril-95% acetonitril in 0.1% trifluoroacetic acid in 7 min., flow: 2 mL/min. The desired $^{18}$F labelled product of example 3 was isolated in a radiochemical purity of >99% and a radiochemical yield of 27.5% corrected for radioactive decay within 70 minutes and confirmed by co-injection with the corresponding non-radioactive F-19 fluoro-standard of example 2.

The eluate was monitored by a UV absorbance detector (λ=254 nm) in series with a radioactivity detector. The retention time of the $^{18}$F labelled product was t$_R$=2.59 min (FIG. 7) and the retention time of the non-radioactive reference compound was determined to be t$_R$=2.36 min (FIG. 8).

Examples Demonstrating the Superior Properties of Compounds of the Present Invention Over Compounds Disclosed in Prior Art

[$^{19}$F] D2 Deprenyl (compound of Example 2) has an affinity towards MAO-B of IC$_{50}$=41.3 nM. This was determined by incubating human MAO-B prepared from insect cells infected with recombinant baculovirus containing respective cDNA inserts (Sigma) with respective reagents of the Amplex Red Monoamine Oxidase Assay-Kit (Molecular Probes). The affinity towards MAO-A is greater than 2 µM.

Figure 1:
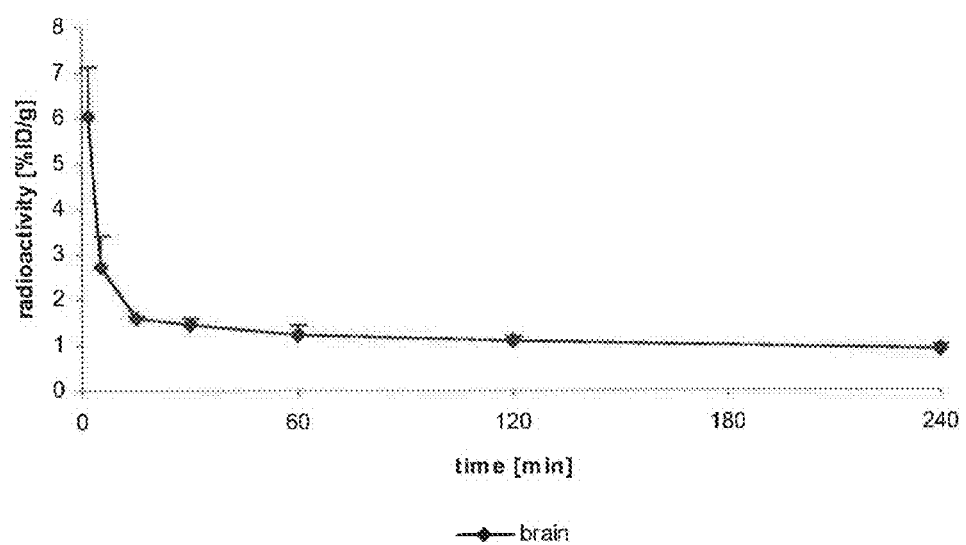
FIG. 1: Distribution of [¹⁸F] D2 Deprenyl (compound of Example 3) detected via a gamma-detector is shown in a time frame of 4 hours in mouse brains (n=3).

Biodistribution of [$^{18}$F] D2 Deprenyl (compound of Example 3) was investigated in NMRI mice weighing 31.1-38.5 g at seven time points. For each time point 3 mice were used. The mice were injected each with 0.256 MBq [$^{18}$F] D2 Deprenyl. After the respective time points the mice were sacrificed, the organs taken out and measured in a gamma counter. The results were decay corrected. The compound showed a high initial brain uptake of radioactivity (Peak: 6.03±1.09% ID/g at 2 min p.i.) and a high initial elimination of radioactivity from the brain (1.44±0.15% ID/g at 30 min p.i.) with a further decrease (0.91±0.09% ID/g, 4 hours p.i.) as shown in FIG. 1. Unexpectedly, the elimination ratio defined by peak uptake at 2 min to uptake at 30 min was 4.2 times. This is improved over the non-deuterated compound where said ratio was 3.6 (Peak: 7.5±0.04% ID/g at 2 min p.i. and 2.10±0.33% ID/g at 30 min p.i.) and will add to a better brain image quality. Therefore, an improved diagnostic performance can be expected.

[$^{18}$F] D2 Deprenyl and [$^{19}$F] D2 Deprenyl have been investigated regarding their metabolic properties in vitro and in vivo. Investigations of the metabolite profile in rat, mouse and human liver microsomes and human and rat hepatocytes show that N-dealkylation is the major metabolic pathway for both the deuterated and the non-deuterated compound. However, oxidation at the propargyl moiety, as observed as an additional metabolic pathway for the non-deuterated compound (M-7), was surprisingly not detectable any more in incubations with [$^{19}$F] D2 Deprenyl (FIG. 9).

Figure 2:
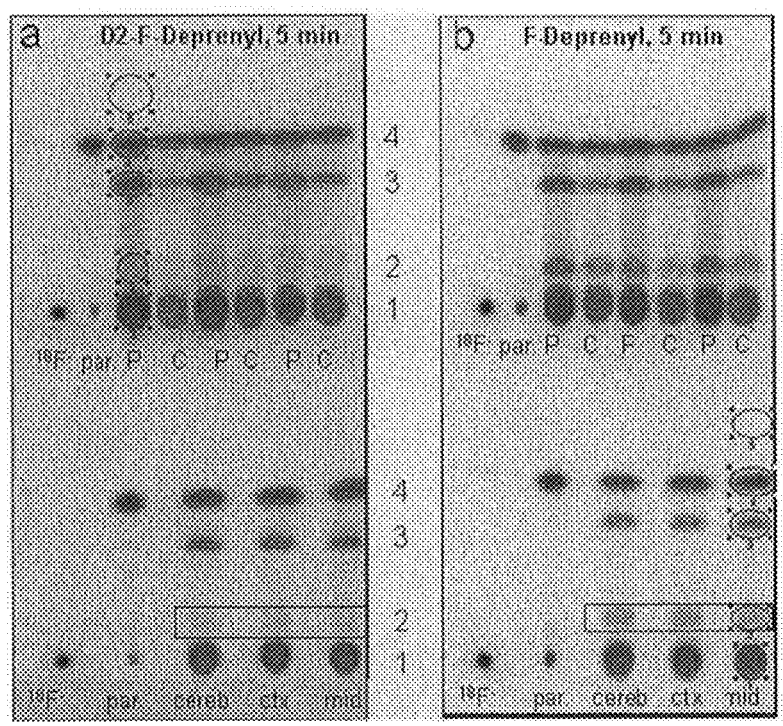
FIG. 2: Autoradiographies of thin layer chromatograms (TLC) generated by using a solvent consisting of 10% hexane/90% ethyl acetate. Mouse plasma, cruor and brain tissue were investigated at 5 min p.i. in order to detect metabolites generated from (a) [¹⁸F] D2 Deprenyl and (b) non-deuterated [¹⁸F] Deprenyl (compound F). Circles delineate the regions of interest (ROI) for measurement of the respective bands by use of the software Image Quant 5.2. The band represented by ROI2 in (a) is reduced in intensity as compared to (b) (marked by a square). ¹⁸F—free fluoride, par.—parent compound, P—plasma, C—cruor (n=3 mice); cereb.—cerebellum, ctx—cortex, mid—midbrain (tissue from 3 mice pooled for each region; 1-[¹⁸F] metamphetamine; 2-[¹⁸F] amphetamine.

In addition, in brain tissue the $^{18}$F metabolite represented by region of interest 2 (ROI2, marked by a square) of the thin layer chromatogram (TLC) was identified as [$^{18}$F] amphetamine (FIG. 2b). Optical density of this metabolite band was measured using the software Image Quant 5.2 (Molecular Dynamics 1999) and revealed a reduction by about 2.4 times for [$^{18}$F] D2 Deprenyl as compared to the non-deuterated [$^{18}$F] Deprenyl (compound F) (FIG. 2a). Specifically, these data hint to an improved metabolism profile of [$^{18}$F] D2 Deprenyl as an advantage over the non-deuterated compound expecting to lead to less background signal in brain PET images.

Plasma radioactivity metabolic profiles have been monitored over time for [$^{18}$F] D2 Deprenyl compared to the non-deuterated [$^{18}$F] Deprenyl in cynomolgus monkey plasma (FIG. 3). As can be seen from the comparison of the graphs depicting the radioactivity of [$^{18}$F] D2 Deprenyl in plasma the radioactivity for [$^{18}$F] D2 Deprenyl was 18% and 31% higher as observed for [$^{18}$F] Deprenyl at the 30 and 60 min time points, respectively (FIG. 3). In addition, metabolites occurring in cynomolgus monkey plasma over time have been monitored for both ligands (FIG. 4). As can be seen from FIG. 3, [$^{18}$F] D2 Deprenyl was more stable in plasma than the non-deuterated [$^{18}$F] Deprenyl. Specifically metabolite M1 was less produced (FIG. 4a). In addition, time activity curves (TAC) of [$^{18}$F] D2 Deprenyl showed features of a reversible behaviour (FIG. 10). This gives more flexibility regarding quantification of the PET data and is, thus, an advantage.

A particularly important improvement of MAO-B imaging is the surprising technical effect that a decrease in signal intensity from [$^{18}$F] Deprenyl towards [$^{18}$F] D2 Deprenyl is between 6-8 times in the brain regions investigated during the steady state phase (see FIG. 5a). From studies using [$^{11}$C] Deprenyl it is known that the MAO-B signal is underestimated in regions with high MAO-B activity due to high trapping rate that is similar to or exceeds delivery (Fowler et al. J Nucl Med 1995, 36: 1255). Deuteration of [$^{11}$C] Deprenyl has been reported to result in a reduced trapping rate leading to more reliable quantification of the signal. The effect of deuteration on the decrease in signal intensity for the [$^{11}$C] D2 Deprenyl (DED) observed in healthy baboon and human brain regions comparable to those investigated by us, e.g. striatum, thalamus, cortex, is only approximately 1.2-2.0 (Fowler et al. J. Neurochem 1988, 51: 1524-1534; J. Nucl. Med. 1995, 36: 1255-1262; Mol. Imaging. Biol. 2005, 7: 377-387). This unexpectedly pronounced improvement of aforementioned ratio (6 to 8 as compared to 1.2 to 2.0 in the prior art) renders the compounds of the invention as superior PET imaging agents.

19. The compound according to claim 1, wherein said compound is:
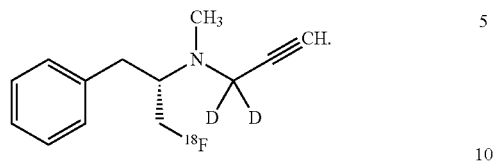

The invention claimed is:

1. A compound of formula I:

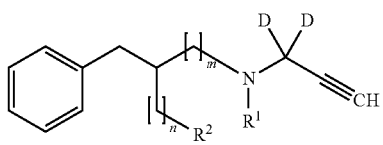

wherein
D is deuterium;
R$^1$ is selected from methyl, ethyl, n-propyl, n-butyl, and iso-butyl;
R$^2$ is [$^{18}$F]fluorine; and
n and m are each selected from 0 and 1;

with the provisos that:
if n=0, m must be 1, and
if n=1, m must be 0;
including all stereoisomeric forms of said compound, including but not limited to enantiomers and diastereoisomers as well as racemic mixtures,
including salts thereof with an organic or inorganic acids.

2. The compound according to claim 1, wherein
D is deuterium;
R$^1$ is methyl; and
R$^2$ is [$^{18}$F]fluorine.

3. The compound according to claim 1, wherein said compound is of formula Ia:

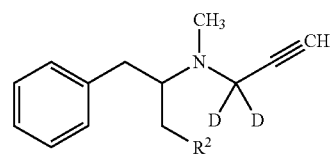

wherein
D is deuterium; and
R$^2$ is [$^{18}$F]fluorine;
including enantiomers as well as racemic mixtures, and any suitable salt with an organic or inorganic acid.

4. The compound according to claim 1, wherein said compound is selected from:
a compound of formula Ic,

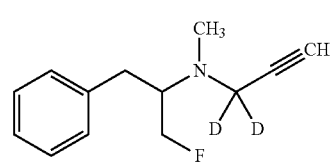

wherein F=$^{18}$F,
a compound of formula Ie,

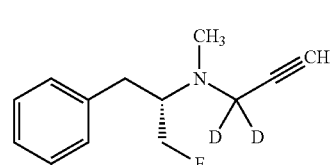

wherein F=$^{18}$F,
and salts thereof with organic or inorganic acids.

5. A diagnostic composition for PET imaging comprising a [$^{18}$F] labelled compound according to claim 1.

6. A method of diagnostic PET imaging comprising subjecting a patient to diagnostic PET imaging of CNS diseases, wherein said patient has been administered an [$^{18}$F] labelled compound according to claim 1.

7. A method of diagnostic PET imaging comprising subjecting a patient to diagnostic PET imaging of CNS diseases, wherein said patient has been administered a diagnostic composition according to claim 5.

8. The method according to claim 6, wherein said patient is imaged for Alzheimer's disease.

9. The method according to claim 6, wherein said [$^{18}$F] labelled compound is a compound of formula Ie:

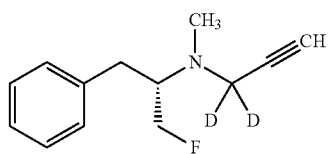

wherein F=$^{18}$F.

10. A method for the synthesis of a compound according to claim 1:

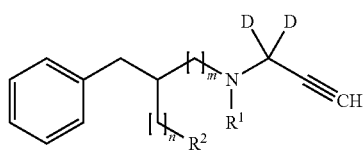

wherein
  D is deuterium;
  R$^1$ is selected from methyl, ethyl, n-propyl, n-butyl, and iso-butyl;
  R$^2$ is [$^{18}$F]fluorine; and
  n is 1 and m is 0;
said method comprising:
  reacting a compound of formula I:

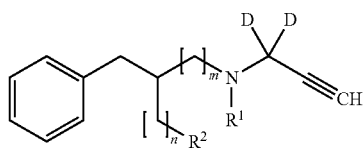

wherein
  D is deuterium;
  R$^1$ is selected from methyl, ethyl, n-propyl, n-butyl, and iso-butyl;
  R$^2$ is leaving group, wherein said leaving group is selected from halogen, C$_1$-C$_6$-alkylsulfonyloxy, which is optionally substituted by fluorine, and arylsulfonyloxy, which is optionally substituted by hydrogen, methyl, halo and nitro;
  n is 0; and
  m is 1;
with a suitable F-fluorinating agent, wherein F is $^{18}$F.

11. The method according to claim 10 for the synthesis of a compound of formula Ic:

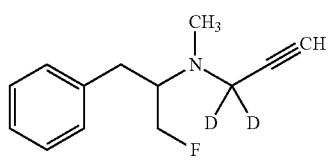

wherein F is $^{18}$F, said method comprising:
  reacting a compound of formula Id:

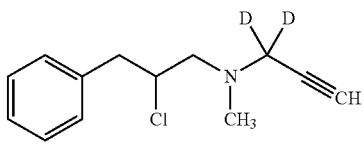

with a suitable F-fluorinating agent, wherein F is $^{18}$F.

12. The method according to claim 10 for the synthesis of a compound of formula Ie:

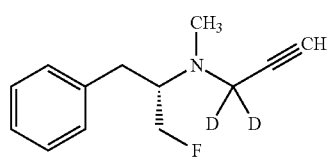

wherein F is $^{18}$F,
said method comprising:
  reacting a compound of formula If:

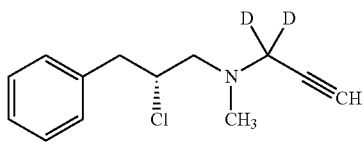

with a suitable F-fluorinating agent, wherein F is $^{18}$F.

13. A kit comprising at least one sealed container comprising a compound according to claim 1.

14. A kit comprising at least one sealed container comprising a compound of claim 4.

15. The kit according to claim 13, further comprising a further sealed container comprising reagents.

16. The compound according to claim 1, wherein n is 0 and m is 1.

17. The compound according to claim 1, wherein n is 1 and m is 0.

18. The compound according to claim 1, wherein said compound is a salt of a compound of formula I with an acid selected from carbonic, nitric, phosphoric, hydrochloric, perchloric, sulfuric, formic, acetic, trifluoracetic, propionic, succinic, glycolic, gluconic, lactic, malic, fumaric, pyruvic, benzoic, anthranilic, mesylic, fumaric, salicylic, phenylacetic, mandelic, embonic, methansulfonic, ethanesulfonic, benzenesulfonic, phantothenic, toluenesulfonic, trifluormethansulfonic and sulfanilic acids.